United States Patent
Humphries et al.

(10) Patent No.: US 9,562,136 B2
(45) Date of Patent: Feb. 7, 2017

(54) POLYMERS, MONOMERS AND METHODS OF FORMING POLYMERS

(75) Inventors: Martin Humphries, Cambridgeshire (GB); Florence Bourcet, Cambridgeshire (GB); Sheena Zuberi, Cambridgeshire (GB)

(73) Assignees: Cambridge Display Technology, Ltd., Godmanchester (GB); Sumitomo Chemical Company Limited, Tokyo (JP)

( * ) Notice: Subject to any disclaimer, the term of this patent is extended or adjusted under 35 U.S.C. 154(b) by 88 days.

(21) Appl. No.: 14/130,920

(22) PCT Filed: Jul. 3, 2012

(86) PCT No.: PCT/GB2012/051552
§ 371 (c)(1),
(2), (4) Date: Apr. 22, 2014

(87) PCT Pub. No.: WO2013/005026
PCT Pub. Date: Jan. 10, 2013

(65) Prior Publication Data
US 2014/0235800 A1  Aug. 21, 2014

(30) Foreign Application Priority Data

Jul. 4, 2011 (GB) .................................. 1111360.2
Jul. 4, 2011 (GB) .................................. 1111372.7
(Continued)

(51) Int. Cl.
C08G 73/02 (2006.01)
C08G 61/12 (2006.01)
(Continued)

(52) U.S. Cl.
CPC ............ *C08G 73/026* (2013.01); *C08G 61/12* (2013.01); *C08L 65/00* (2013.01);
(Continued)

(58) Field of Classification Search
CPC ...................................................... C08G 61/02
(Continued)

(56) References Cited

U.S. PATENT DOCUMENTS 4,540,763 A * 9/1985 Kirchhoff ............... C07C 2/861
526/281
4,567,181 A   1/1986 Malen et al.
(Continued)

FOREIGN PATENT DOCUMENTS

EP   0402975 A2   12/1990
EP   2 308 910 A1   4/2011
(Continued)

OTHER PUBLICATIONS

International Search Report and Written Opinion for International Application No. PCT/GB2012/051552 dated Jan. 30, 2013.
(Continued)

*Primary Examiner* — Mike M Dollinger
(74) *Attorney, Agent, or Firm* — Wolf, Greenfield & Sacks, P.C.

(57) ABSTRACT

A method of forming a crosslinked polymer comprising the step of reacting a crosslinkable group in the presence of a polymer, wherein: the crosslinkable group comprises a core unit substituted with at least one crosslinkable unit of formula (I): the crosslinkable group is bound to the polymer or is a crosslinkable compound mixed with the polymer; Ar is aryl or heteroaryl which may be unsubstituted or substituted with one or more substituents independently selected from monovalent substituents and a divalent linking group
(Continued)

linking the unit of formula (I) to the core unit; and R is independently in each occurrence H, a monovalent substituent or a divalent linking group linking the unit of formula (I) to the core unit, with the proviso that at least one R is not H.

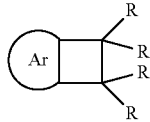

(I)

15 Claims, 1 Drawing Sheet

(30) Foreign Application Priority Data

Jul. 4, 2011 (GB) .................................... 1111375.0
Nov. 22, 2011 (GB) .................................... 1120131.6

(51) Int. Cl.
   *C08L 65/00* (2006.01)
   *H01L 51/00* (2006.01)
   *H01L 51/50* (2006.01)

(52) U.S. Cl.
   CPC ...... *H01L 51/0007* (2013.01); *H01L 51/0043* (2013.01); *H01L 51/5016* (2013.01); *H01L 51/5044* (2013.01); *C08G 2261/12* (2013.01); *C08G 2261/135* (2013.01); *C08G 2261/141* (2013.01); *C08G 2261/1414* (2013.01); *C08G 2261/1434* (2013.01); *C08G 2261/312* (2013.01); *C08G 2261/3142* (2013.01); *C08G 2261/3221* (2013.01); *C08G 2261/374* (2013.01); *H01L 51/0039* (2013.01); *H01L 51/0085* (2013.01); *H01L 51/5004* (2013.01)

(58) Field of Classification Search
   USPC ....................................................... 525/539
   See application file for complete search history.

(56) References Cited

U.S. PATENT DOCUMENTS

| | | | |
|---|---|---|---|
| 4,638,078 A | 1/1987 | Kirchhoff | |
| 4,642,329 A * | 2/1987 | Kirchhoff | C07C 13/44 526/284 |
| 4,831,172 A * | 5/1989 | Hahn | C07F 7/1836 257/E21.505 |
| 5,387,725 A * | 2/1995 | Walters | C07B 37/04 562/480 |
| 5,585,450 A * | 12/1996 | Oaks | C07C 247/16 526/279 |
| 6,462,207 B1 | 10/2002 | Sedaghat-Herati | |
| 7,893,160 B2 * | 2/2011 | Inbasekaran | C07C 25/22 257/40 |
| 2002/0076535 A1 | 6/2002 | Cooray | |
| 2007/0096082 A1* | 5/2007 | Gaynor | C07C 211/60 257/40 |
| 2007/0099026 A1 | 5/2007 | Lee et al. | |
| 2007/0228938 A1 | 10/2007 | Hatwar et al. | |
| 2008/0169756 A1 | 7/2008 | Son et al. | |
| 2009/0045739 A1 | 2/2009 | Kho et al. | |
| 2009/0226757 A1 | 9/2009 | Song et al. | |
| 2010/0062643 A1 | 3/2010 | Kumagai et al. | |
| 2010/0090238 A1 | 4/2010 | Mori et al. | |
| 2010/0163854 A1 | 7/2010 | Kho et al. | |
| 2010/0270539 A1 | 10/2010 | Nishimura et al. | |
| 2012/0306358 A1 | 12/2012 | Hirano et al. | |

FOREIGN PATENT DOCUMENTS

| | | |
|---|---|---|
| EP | 2 518 111 A1 | 10/2012 |
| EP | 2 520 576 A1 | 11/2012 |
| JP | S59-139361 A | 8/1984 |
| JP | S61-064720 A | 4/1986 |
| JP | S61-501572 A | 7/1986 |
| JP | S61-501576 A | 7/1986 |
| JP | S64-062207 A | 3/1989 |
| JP | H03-081253 A | 4/1991 |
| JP | 2002-138248 A | 5/2002 |
| JP | 2003-285570 | 10/2003 |
| JP | 2003-287882 | 10/2003 |
| JP | 2011-049058 A | 3/2011 |
| WO | WO 86/01503 A1 | 3/1986 |
| WO | WO 2005/049689 A2 | 6/2005 |
| WO | WO 2008/024435 A2 | 2/2008 |
| WO | WO 2008/025997 A1 | 3/2008 |
| WO | WO 2010/115498 A1 | 10/2010 |
| WO | WO 2011/078391 A1 | 6/2011 |

OTHER PUBLICATIONS

Combined Search and Examination Report for Application No. GB1120131.6 dated Mar. 22, 2012.
Combined Search and Examination Report for Application No. GB1111360.2 dated Oct. 31, 2011.
Combined Search and Examination Report for Application No. GB1111372.7 dated Nov. 9, 2011.
Combined Search and Examination Report for Application No. GB1111375.0 dated Mar. 5, 2012.
International Search Report and Written Opinion for International Application No. PCT/GB2012/051555 dated Nov. 14, 2012.
Chino et al., Synthesis of a Poly(vinyl ether) Containing a Benzocyclobutene Moiety and its Reaction with Dienophiles. J Polym Sci Part A: Polym Chem. 1999;37(1):59-67.

* cited by examiner

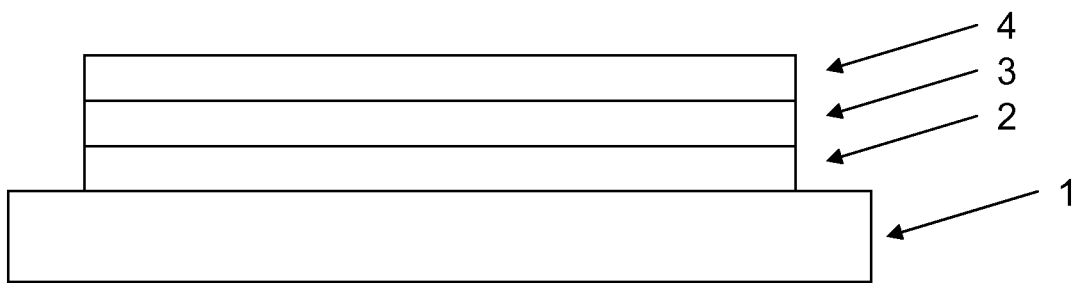

POLYMERS, MONOMERS AND METHODS OF FORMING POLYMERS

RELATED APPLICATIONS

The present application is a national stage filing under 35 U.S.C. §371 of international PCT application, PCT/GB2012/051552, filed Jul. 3, 2012, which claims priority to United Kingdom patent application, GB 1120131.6, filed Nov. 22, 2011, United Kingdom patent application, GB 1111375.0, filed Jul. 4, 2011, United Kingdom patent application, GB 1111372.7, filed Jul. 4, 2011 and United Kingdom patent application, GB 1111360.2, filed Jul. 4, 2011, each of which is incorporated herein by reference.

SUMMARY OF THE INVENTION

The present invention relates to materials and methods of forming polymers, including crosslinked polymers, and uses thereof.

BACKGROUND

Electronic devices comprising active organic materials are attracting increasing attention for use in devices such as organic light emitting diodes (OLEDs), organic photoresponsive devices (in particular organic photovoltaic devices and organic photosensors), organic transistors and memory array devices. Devices comprising organic materials offer benefits such as low weight, low power consumption and flexibility. Moreover, use of soluble organic materials allows use of solution processing in device manufacture, for example inkjet printing or spin-coating.

An OLED may comprise a substrate carrying an anode, a cathode and one or more organic light-emitting layers between the anode and cathode. One or more organic charge transporting and/or one or more charge blocking layers may also be provided between the anode and cathode.

Holes are injected into the device through the anode and electrons are injected through the cathode during operation of the device. Holes in the highest occupied molecular orbital (HOMO) and electrons in the lowest unoccupied molecular orbital (LUMO) of a light-emitting material combine to form an exciton that releases its energy as light.

Suitable light-emitting materials include small molecule, polymeric and dendrimeric materials. Suitable light-emitting polymers include poly(arylene vinylenes) such as poly (p-phenylene vinylenes) and polyarylenes such as polyfluorenes.

A light emitting layer may comprise a semiconducting host material and a light-emitting dopant wherein energy is transferred from the host material to the light-emitting dopant. For example, J. Appl. Phys. 65, 3610, 1989 discloses a host material doped with a fluorescent light-emitting dopant (that is, a light-emitting material in which light is emitted via decay of a singlet exciton) and Appl. Phys. Lett., 2000, 77, 904 discloses a host material doped with a phosphorescent light emitting dopant (that is, a light-emitting material in which light is emitted via decay of a triplet exciton).

Formation of the one or more organic layers of an OLED may be by deposition of materials used to form those layers from a solution in a solvent followed by evaporation of the solvent. Examples of suitable solution processing methods include coating methods such as spin-coating or dip-coating and printing methods such as inkjet printing or roll-to-roll printing.

In devices comprising multiple organic layers, a first deposited organic layer may be rendered insoluble by crosslinking prior to deposition of a further organic layer by a solution processing method in order to prevent dissolution of the first deposited layer by the solvent used in formation by solution processing of the further organic layer.

WO 2005/049689 discloses polymers comprising fluorene repeat units substituted with crosslinkable groups, including a double bond, a triple bond, a precursor capable of in situ formation of a double bond or a heterocyclic, addition polymerisable group. Benzocyclobutane (BCB) is disclosed as an exemplary crosslinkable group.

WO 2010/013723 discloses polymers comprising double bond groups and BCB groups.

Mariet et al, Tetrahedron 60, 2004, 2829-2835 discloses calculated formation energies for formation of xylylenes from corresponding benzocyclobutanes.

SUMMARY OF THE INVENTION

In a first aspect, the invention provides a method of forming a crosslinked polymer comprising the step of reacting a crosslinkable group in the presence of a polymer, wherein:

the crosslinkable group comprises a core unit substituted with at least one crosslinkable unit of formula (I):

(I)

the crosslinkable group is bound to the polymer or is a crosslinkable compound mixed with the polymer;
Ar is aryl or heteroaryl which may be unsubstituted or substituted with one or more substituents independently selected from monovalent substituents and a divalent linking group linking the unit of formula (I) to the core unit; and
R is independently in each occurrence H, a monovalent substituent or a divalent linking group linking the unit of formula (I) to the core unit, with the proviso that at least one R is not H.

Optionally, Ar is phenyl.
Optionally, the at least one unit of formula (I) has formula (Ia):

(Ia)

Optionally, at least one R is an electron-donating group.
Optionally, at least one R is selected from the group consisting of linear or branched $C_{1-20}$ alkyl; $C_{1-20}$ alkoxy; aryl or heteroaryl, for example phenyl, that is unsubstituted or substituted with one or more substituents, for example one or more C1-10 alkyl groups; and substituted silicon, for example tri(hydrocarbyl)silyl wherein hydrocarbyl is optionally in each occurrence selected from $C_{1-10}$ alkyl, unsubstituted phenyl and phenyl substituted with one or more $C_{1-10}$ alkyl groups. Preferably, at least one R is selected from the group consisting of linear or branched $C_{1-20}$ alkyl or $C_{1-20}$ alkoxy.

In the case where at least one R is aryl or heteroaryl, the aryl or heteroaryl group may be substituted with one or more electron-withdrawing groups. Exemplary electron-withdrawing groups include fluorine and $C_{1-5}$ fluoroalkyl, in particular $C_{1-5}$ perfluoroalkyl such as trifluoromethyl.

Optionally, only one R is not H.

Optionally, the unit of formula (I) has formula (Ib):

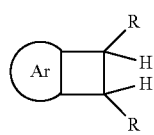

(Ib)

Optionally, the crosslinkable group comprises only one unit of formula (I).

Optionally, the crosslinkable group comprises at least two units of formula (I).

Optionally, the crosslinkable group is a crosslinkable compound mixed with the polymer in the composition.

Optionally, the crosslinkable compound is a compound of formula (IIa) or (IIb):

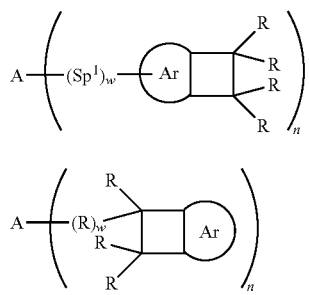

(IIa)

(IIb)

wherein A represents the core unit; $Sp^1$ represents a spacer group; n is at least 2; w in each occurrence is independently 0 or 1; and $Sp^1$, Ar and R in each occurrence may be the same or different.

Optionally, A is an optionally substituted hydrocarbyl group, for example an alkyl, aryl or alkylaryl group, optionally $-CH_{(4-n)}-$.

Optionally, $Sp^1$ is selected from the group consisting of a $C_{1-20}$ n-alkyl chain and an optionally substituted aryl or heteroaryl, and wherein one or more non-adjacent C atoms of the n-alkyl chain may be replaced with substituted or unsubstituted aryl or heteroaryl, O, S, substituted N, substituted Si, $-C=O$ and $-COO-$, and one or more H atoms of the n-alkyl chain may be replaced with $C_{1-5}$ alkyl, F or an aryl or heteroaryl group.

Optionally, the crosslinkable group is covalently bound to the polymer.

Optionally, the crosslinkable group is a repeat unit of the polymer.

Optionally, the repeat unit has formula (IIIa) or (IIIb):

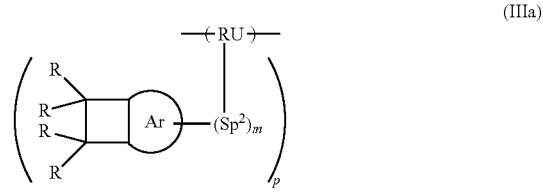

(IIIa)

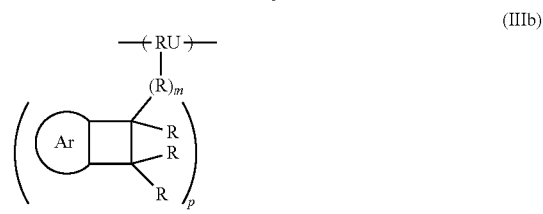

(IIIb)

wherein RU represents a core repeat unit comprised in a backbone of the polymer; $Sp^2$ represents a spacer group; m is 0 or 1; and p is at least 1, optionally 1 or 2.

Optionally, RU represents a conjugated group.

Optionally, RU is at least partially conjugated to one or both adjacent repeat units.

Optionally, RU has formula (XV):

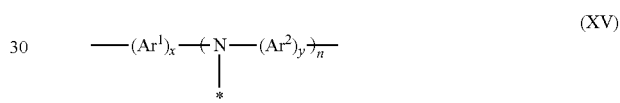

(XV)

wherein $Ar^1$ and $Ar^2$ in each occurrence are independently selected from optionally substituted aryl or heteroaryl, n is greater than or equal to 1, preferably 1 or 2, x and y are each independently 1, 2 or 3; * represents a bond to $Sp^2$, Ar or R; and $Ar^1$ and $Ar^2$ are optionally linked by a direct bond or divalent linking group.

Optionally, RU has formula (XVI):

(XVI)

wherein $Ar^6$ represents a substituted or unsubstituted aryl or heteroaryl group and * represents a bond to $Sp^2$, Ar or R.

Optionally, $Ar^6$ is selected from the group consisting of phenyl, fluorene and indenofluorene, each of which may be substituted or unsubstituted.

Optionally, the repeat unit of formula (IIIa) or (IIIb) has formula (IIIc):

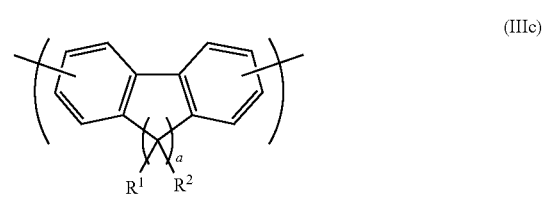

(IIIc)

wherein $R^1$ and $R^2$ are independently in each occurrence H or a substituent with the proviso that at least one of $R^1$ and $R^2$ has formula $-(Sp^2)_m$-XL; XL is a crosslinkable unit of formula (I); and a is at least 1, optionally 1, 2 or 3.

Optionally, the repeat unit of formula (IIIa) or (IIIb) has formula (IIId):

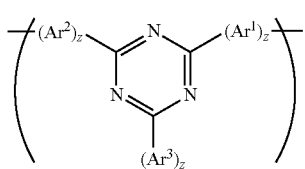

(IIId)

wherein $Ar^1$, $Ar^2$ and $Ar^3$ are each independently selected from a substituted or unsubstituted aryl or heteroaryl group, z in each occurrence is at least 1, and at least one group $Ar^3$ is substituted with at least one substituent of formula $-(Sp^2)_m$-XL wherein XL is a crosslinkable unit of formula (I).

Optionally, $Sp^2$ is selected from the group consisting of a $C_{1-20}$ n-alkyl chain and an optionally substituted aryl or heteroaryl, and wherein one or more non-adjacent C atoms of the n-alkyl chain may be replaced with optionally substituted aryl or heteroaryl, O, S, substituted N, substituted Si, —C=O and —COO—, and one or more H atoms of alkyl may be replaced with $C_{1-5}$ alkyl, F or an aryl or heteroaryl group.

Optionally, the reaction is performed by heating the reactants or exposing the reactants to UV light.

Optionally, the reaction is performed at a temperature of less than 180° C., optionally less than 160° C.

Optionally, the crosslinkable group is provided in the composition in an amount up to 25 mol %, optionally in the range 2.5 mol %-25 mol %.

In a second aspect, the invention provides a monomer of formula (IVa) or (IVb):

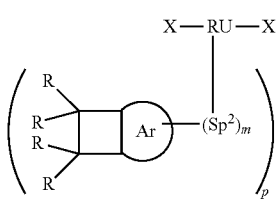

(IVa)

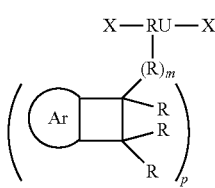

(IVb)

wherein RU $Sp^2$, m and p are as defined in the first aspect and X is independently a polymerisable group.

Optionally, each X is independently a leaving group capable of participating in a transition metal-mediated cross-coupling polymerisation.

Optionally, each X is independently selected from the group consisting of halogen, boronic acids and boronic esters.

In a third aspect, the invention provides a method of forming a crosslinkable polymer comprising the step of polymerizing a monomer according to the second aspect.

Optionally, the monomer of formula (IVa) or (IVb) is polymerized in the presence of at least one co-monomer.

In a fourth aspect, the invention provides a polymer comprising a repeat unit of formula (IIIa) or (IIIb):

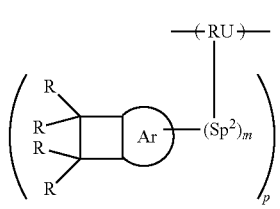

(IIIa)

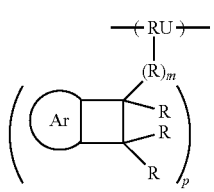

(IIIb)

wherein RU, $Sp^2$, m and p are as defined in the first aspect.

Optionally according to the fourth aspect, the polymer is a copolymer comprising at least one co-repeat unit.

Crosslinkable polymers of the fourth aspect may be used in the method of the first aspect.

In a fifth aspect, the invention provides a compound of formula (XIII):

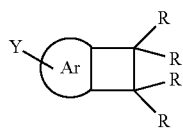

(XIII)

wherein Ar and R are as defined in the first aspect and Y is a leaving group.

Optionally, Y is a halogen, preferably bromine or iodine.

Compounds of formula (XIII) may be reacted through the Ar—Y bond to form a crosslinkable polymer that may be used as described in the first aspect of the invention.

In a sixth aspect, the invention provides a compound of formula (IIa) or (IIb):

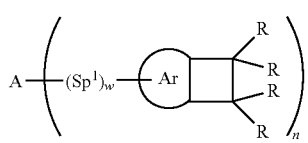

(IIa)

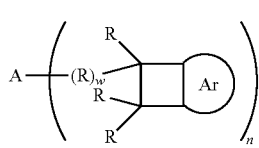

(IIb)

wherein Ar is aryl or heteroaryl which may be the same or different in each occurrence, and which in each occurrence may be unsubstituted or substituted with one or more substituents; R is independently in each occurrence H, a monovalent substituent or a divalent linking group linking the unit of formula (I) to the core unit, with the proviso that at least one R is not H; A represents a core unit; $Sp^1$ represents a spacer group which may be the same or different in each occurrence; n is at least 2; and w in each occurrence is independently 0 or 1.

Optionally according to the sixth aspect, A is selected from the group consisting of —$CH_{(4-n)}$ and a group comprising at least one dienophile.

Optionally according to the sixth aspect, $Sp^1$ is selected from the group consisting of a $C_{1-20}$ n-alkyl chain and an optionally substituted aryl or heteroaryl, and wherein one or more non-adjacent C atoms of the n-alkyl chain may be replaced with substituted or unsubstituted aryl or heteroaryl, O, S, substituted N, substituted Si, —C═O and —COO—, and one or more H atoms of alkyl may be replaced with $C_{1-5}$ alkyl, F or an aryl or heteroaryl group.

In a seventh aspect, the invention provides a method of forming a polymer comprising the step of polymerizing a compound according to the sixth aspect. The polymer formed by the seventh aspect may or may not be crosslinked. If n=2 and if the compound of formula (IIa) or (IIb) is polymerized with a monomer containing only two reactive groups, for example two dienophile groups, then the polymer may be substantially without crosslinking. If n is greater than or equal to 3 and/or if the compound of formula (IIa) or (IIb) is polymerized with a monomer containing 3 or more reactive groups then the polymer formed may be crosslinked.

The compound of formula (IIa) or (IIb) may be polymerized alone or in the presence of at least one co-monomer, for example a co-monomer comprising dienophile groups.

DESCRIPTION OF THE DRAWINGS

The invention will now be described in more detail with reference to the drawings, in which:

FIG. 1 is a schematic illustration of an OLED according to an embodiment of the invention.

DETAILED DESCRIPTION OF THE INVENTION

FIG. 1, which is not drawn to any scale, illustrates schematically an OLED according to an embodiment of the invention. The OLED is carried on substrate 1 and comprises an anode 2, a cathode 4, and a light-emitting layer 3 between the anode and the cathode.

The OLED may be provided with one or more additional layers (not shown) between the anode and the cathode, including one or more further light-emitting layers and/or one or more charge transporting layers, charge blocking layers and/or exciton blocking layers. A plurality of light-emitting layers, in particular two or three light-emitting layers, may be provided to form an OLED that emits white light.

The light-emitting layer 3, and any further organic charge transporting and/or light-emitting layers, may be crosslinked.

One or more organic layers of the OLED may be crosslinked prior to formation of an overlying layer deposited from a solution. This may serve to prevent the solvent or solvents of the solution causing dissolution of an uncrosslinked layer. For example, a hole-transporting layer formed over anode 2 may be crosslinked prior to formation of a light-emitting layer 3 overlying anode 2. A light-emitting layer may likewise be crosslinked. For example, if a plurality of light-emitting layers is present (for example two or more light-emitting layers that together produce white light) then a light-emitting layer may be crosslinked prior to deposition of an overlying light-emitting layer.

Crosslinkable Compositions

Crosslinkable compositions may contain a polymer and a crosslinkable group. The crosslinkable group may comprise one or more types of crosslinkable units, at least one of which has of formula (I).

The crosslinkable group may be covalently bound to the polymer backbone, or the crosslinkable group may be a separate compound mixed with the polymer.

In the case where the crosslinkable group is covalently bound to the polymer backbone, the crosslinkable group may be a polymeric end-group or polymeric repeat unit substituted with one or more crosslinkable units of formula (I). The one or more crosslinkable units of formula (I) may be bound directly to said end-group or polymeric repeat unit, or spaced apart from said end-group or polymeric repeat unit by a respective one or more spacer groups.

Exemplary Spacer Groups Include:

optionally substituted aryl or heteroaryl groups, for example phenyl groups optionally substituted with one or more $C_{1-10}$ alkyl groups; and a $C_{1-20}$ n-alkyl chain wherein one or more non-adjacent C atoms of the n-alkyl chain may be replaced with optionally substituted aryl or heteroaryl, O, S, substituted N, substituted Si—C═O and —COO—, and one or more H atoms of the n-alkyl chain may be replaced with $C_{1-5}$ alkyl, F or an aryl or heteroaryl group. Exemplary substituents for substituted N and substituted Si include $C_{1-10}$ alkyl. Where a C atom is replaced with an aryl or heteroaryl group, the aryl or heteroaryl group is preferably phenyl optionally substituted with one or more $C_{1-10}$ alkyl groups.

Preferred spacer groups include branched or linear $C_{1-20}$ alkyl and phenylalkyl.

A crosslinkable unit of formula (I) may be bound to a repeat unit in the polymer backbone, directly or through a spacer group, through any atom of the crosslinkable unit. In one arrangement, a crosslinkable unit of formula (I) is bound to the polymer through an aromatic ring atom of the group Ar of formula (I). In another arrangement, a crosslinkable unit of formula (I) is bound to the polymer through one of the $sp^3$-hybridised carbon atoms of the cyclobutyl group of formula (I), either directly or through a divalent linking group R. In this case, the cyclobutyl group may carry no further substituents, or may carry one or more monovalent substituents R in addition to divalent linking group R.

The crosslinkable units of formula (I) may be bound to the polymer backbone after formation of the polymer, however it is preferred that the monomers used to form the polymer comprise crosslinkable units of formula (I). The molar percentage of monomers used to form a polymer comprising crosslinkable units of formula (I), and the molar percentage of polymeric repeat units comprising crosslinkable units of formula (I) in the polymer, is optionally up to 25 mol %, for example in the range of 2.5-25 mol %.

In the case where the crosslinkable group is a separate compound from the polymer, the compound may have a core group, for example a C atom or a phenyl group, with two or more crosslinkable units attached to the core group through respective two or more spacer groups. The spacer groups for such a compound may be selected from spacer groups described above. The polymer may be provided with groups capable of reacting with the crosslinkable units of the crosslinkable compound such that, upon crosslinking, the polymer is covalently bound to the compound comprising crosslinkable units of formula (I). Alternatively, the polymer may be substantially free of groups capable of reacting with the crosslinkable units of the crosslinkable compound in which case crosslinking of the compound may produce an interpenetrating network of the polymer and the crosslinked compound.

In one arrangement, a crosslinkable unit of formula (I) is bound to a spacer group of a compound or a polymer repeat unit, or to a polymer backbone, through an aromatic ring atom of the group Ar of formula (I). In another arrangement, a crosslinkable unit of formula (I) is bound a spacer group of a compound or a polymer repeat unit, or to a polymer backbone, through one of the sp$^3$-hybridised carbon atoms of the cyclobutyl group of formula (I).

In one arrangement, all or substantially all crosslinkable units in the composition may be units of formula (I). In another arrangement, the crosslinkable composition may contain crosslinkable units other than units of formula (I), for example crosslinkable units having formula (I) but wherein each R is H, and/or crosslinkable units containing an unsaturated carbon-carbon bond.

Examples of crosslinkable units containing an unsaturated carbon-carbon bond include units of formula (V):

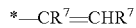   (V)

wherein R$^7$ independently in each occurrence is H or a substituent, and * indicates attachment of the unit to H or a substituent, or attachment of the unit to a polymer.

A unit of formula (V) may be bound directly to a polymer backbone, or may be spaced apart from the backbone by a spacer group, for example a C$_{1-20}$ alkyl chain.

Exemplary substituents R$^7$ include C$_{1-20}$ alkyl and optionally substituted aryl or heteroaryl, for example phenyl substituted with one or more C$_{1-20}$ alkyl groups. In one preferred embodiment, each R$^7$ is H. In another preferred embodiment, one R$^7$ is H and the other R$^7$ is a substituent.

The cyclobutane ring of formula (I) may ring-open to form a diene that is capable of reacting with a dienophile in a Diels-Alder reaction. The dienophile may be, for example, a crosslinkable unit of formula (V).

An example of a compound comprising a crosslinkable unit of formula (I) is illustrated below:

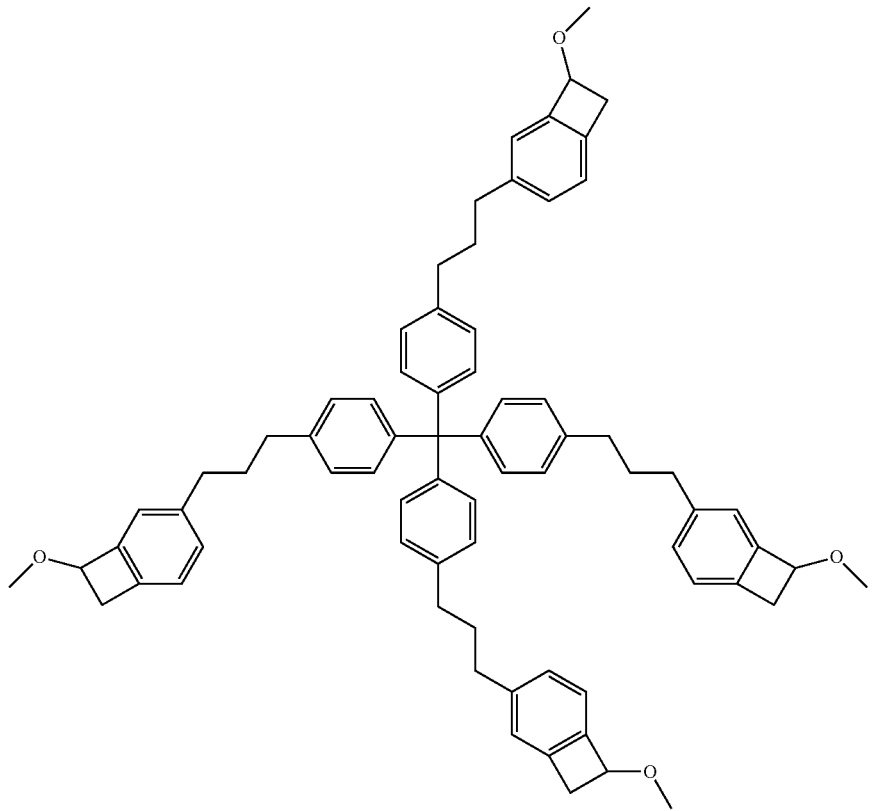

Examples of repeat units substituted with a crosslinkable unit of formula (I) are illustrated below:

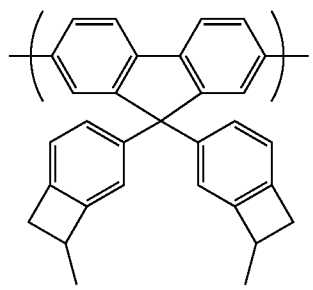

-continued

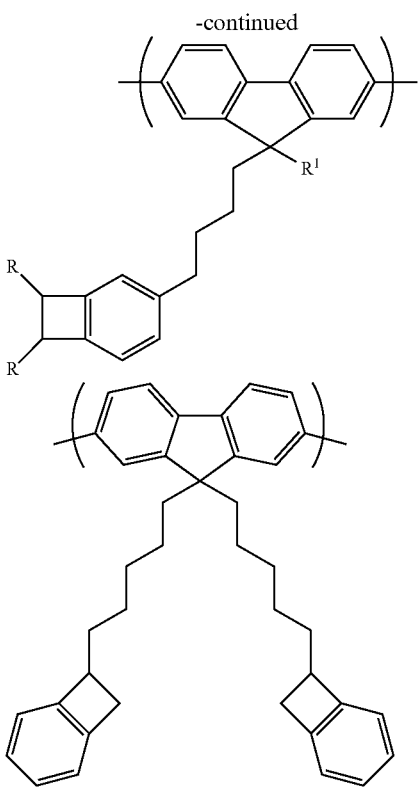

wherein R is as described above with reference to Formula (I) and $R^1$ is as described below with reference to Formula (VII).

The number, substitution position and identity of substituents R in a crosslinkable unit of formula (I) may be selected according to the effect that the substituent has on the crosslinking reactivity of the crosslinkable unit. For example, a substituent R such as alkoxy, that causes a large increase in crosslinking reactivity of the crosslinkable unit, enabling very low temperature (e.g. <100° C.) crosslinking may be suitable for use where that crosslinkable unit is provided in a compound that is mixed with the polymer. On the other hand, in the case where a monomer comprising one or more crosslinkable units of formula (I) is polymerized it may be preferable to provide a substituent R that provides for lower temperature crosslinking as compared to an unsubstituted cyclobutane, but without lowering the crosslinking temperature to such a level that crosslinking takes place during polymerisation of the monomer. For example, alkyl substituents may be suitable substituents R in a monomer comprising one or more crosslinkable units of formula (I).

Crosslinking Conditions

The crosslinking groups may be crosslinked by, for example, thermal treatment and/or exposure to light (e.g. UV light) having a wavelength and intensity for crosslinking. Crosslinking by thermal treatment may be at a temperature up to about 180° C., optionally up to about 160° C., optionally up to about 140° C. or 120° C. The treatment time may be up to about 60 minutes. The treatment time may depend on the treatment temperature. For example, a treatment at a temperature above 180° C. may be suitable if conducted for less than about 10 minutes.

The device may be exposed to one or more further heat treatment steps in addition to a thermal crosslinking treatment. Further heat treatment steps include annealing of a hole injection layer prior to formation of overlying layers and, if the inventive method is used to crosslink a hole transporting layer, annealing of the light-emitting layer(s) before and/or after formation of the cathode. Heat treatment steps following crosslinking according to the invention may be at a temperature of no more than 180° C., optionally no more than 160° C., optionally no more than 140° C. or 120° C.

Polymer

In the case where the invention is applied in the field of organic electronic devices, for example organic light-emitting devices, the polymer, which may be a homopolymer or a copolymer comprising two or more different repeat units, may be at least partially conjugated along its backbone.

The polymer may contain crosslinkable groups in the form of polymeric repeat units, wherein each such repeat unit comprises a core in the polymer backbone substituted with one or more crosslinkable units of formula (I).

Exemplary repeat units of a conjugated polymer include, without limitation, units as described in (i)-(iv) below, each of which may be substituted with one or more crosslinkable units of formula (I).

Each of repeat units (i)-(iv) may contain no crosslinkable unit; one or more crosslinkable units other than a crosslinkable unit of formula (I), such as a group comprising a terminal double bond, for example a crosslinkable group comprising a unit of formula (V); or at least one crosslinkable unit of formula (I).

Where a repeat unit does not contain a crosslinkable unit of formula (I), this unit may be provided as a substituent of another repeat unit of the polymer, and/or in a compound mixed with the polymer.

(i) Optionally substituted (hetero)arylamine repeat units, for example repeat units of formula (VI):

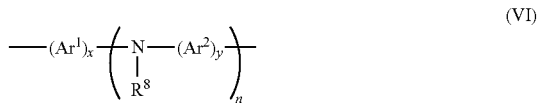

wherein $Ar^1$ and $Ar^2$ in each occurrence are independently selected from optionally substituted aryl or heteroaryl groups, n is greater than or equal to 1, preferably 1 or 2, $R^8$ is H or a substituent, preferably a substituent, and x and y are each independently 1, 2 or 3.

$R^8$, which may be the same or different in each occurrence when n>1, is preferably selected from the group consisting of alkyl, for example $C_{1-20}$ alkyl, $Ar^3$, a branched or linear chain of $Ar^3$ groups, or a crosslinkable unit that is bound directly to the N atom of formula (VI) or spaced apart therefrom by a spacer group, wherein $Ar^3$ in each occurrence is independently optionally substituted aryl or heteroaryl. Exemplary spacer groups are as described above, for example $C_{1-20}$ alkyl, phenyl and phenyl-$C_{1-20}$ alkyl.

$Ar^3$ groups may be substituted with one or more substituents as described below. An exemplary branched or linear chain of $Ar^3$ groups may have formula $—(Ar^3)_r$, wherein $Ar^3$ in each occurrence is independently selected from aryl or heteroaryl and r is at least 1, optionally 1, 2 or 3. An exemplary branched chain of $Ar^3$ groups is 3,5-diphenylbenzene.

In the case where $R^8$ contains a crosslinkable unit, the crosslinkable unit may or may not be a unit of formula (I). If the crosslinkable unit is not a unit of formula (I) then the crosslinkable unit may be a unit that reacts with a unit of formula (I) that may be provided as a substituent of another repeat unit of the polymer, or in a compound mixed with the polymer.

Any of $Ar^1$, $Ar^2$ and $Ar^3$ may independently be substituted with one or more substituents. Preferred substituents are selected from the group $R^3$ consisting of:
  alkyl, for example $C_{1-20}$ alkyl, wherein one or more non-adjacent C atoms may be replaced with O, S, substituted N, C=O and —COO— and one or more H atoms of the alkyl group may be replaced with F or aryl or heteroaryl optionally substituted with one or more groups $R^4$,
  aryl or heteroaryl optionally substituted with one or more groups $R^4$,
  $NR^5_2$, $OR^5$, $SR^5$,
  fluorine, nitro and cyano;
wherein each $R^4$ is independently alkyl, for example $C_{1-20}$ alkyl, in which one or more non-adjacent C atoms may be replaced with O, S, substituted N, C=O and —COO— and one or more H atoms of the alkyl group may be replaced with F, and each $R^5$ is independently selected from the group consisting of alkyl and aryl or heteroaryl optionally substituted with one or more alkyl groups.

Any of $Ar^1$, $Ar^2$ and, if present, $Ar^3$ in the repeat unit of Formula (VI) may be linked by a direct bond or a divalent linking atom or group to another of $Ar^1$, $Ar^2$ and $Ar^3$. Preferred divalent linking atoms and groups include O, S; substituted N; and substituted C.

Where present, substituted N or substituted C of $R^3$, $R^4$ or of the divalent linking group may independently in each occurrence be $NR^6$ or $CR^6_2$ respectively wherein $R^6$ is alkyl or optionally substituted aryl or heteroaryl. Optional substituents for aryl or heteroaryl groups $R^6$ may be selected from $R^4$ or $R^5$.

In one preferred arrangement, $R^8$ is $Ar^3$ and each of $Ar^1$, $Ar^2$ and $Ar^3$ are independently and optionally substituted with one or more $C_{1-20}$ alkyl groups.

Particularly preferred units satisfying Formula (VI) include units of Formulae 1-3:

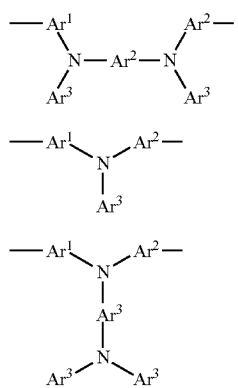

wherein $Ar^1$ and $Ar^2$ are as defined above; and $Ar^3$ is optionally substituted aryl or heteroaryl. Where present, preferred substituents for $Ar^3$ include substituents as described for $Ar^1$ and $Ar^2$, in particular alkyl and alkoxy groups.

$Ar^1$, $Ar^2$ and $Ar^3$ are preferably phenyl, each of which may independently be substituted with one or more substituents as described above.

In another preferred arrangement, aryl or heteroaryl groups of formula (VI) are phenyl, each phenyl group being optionally substituted with one or more alkyl groups.

In another preferred arrangement, $Ar^1$, $Ar^2$ and $Ar^3$ are phenyl, each of which may be substituted with one or more $C_{1-20}$ alkyl groups, and r=1.

In another preferred arrangement, $Ar^1$ and $Ar^2$ are phenyl, each of which may be substituted with one or more $C_{1-20}$ alkyl groups, and $R^8$ is 3,5-diphenylbenzene wherein each phenyl may be substituted with one or more alkyl groups.

In another preferred arrangement, n, x and y are each 1 and $Ar^1$ and $Ar^2$ are phenyl linked by an oxygen atom to form a phenoxazine ring.

In the case where the repeat unit of formula (VI) is provided as a repeat unit of a copolymer, the repeat units of formula (VI) may make up 0.1-99 mol % of the copolymer's repeat units. In the case where the copolymer is for use as a light-emitting polymer or hole-transporting polymer, the repeat units of formula (VI) may be provided in an amount of less than 50 mol %, optionally less than 20 mol %.

(ii) Optionally substituted (hetero)arylene repeat units, for example phenyl, fluorene and indenofluorene repeat units, each of which may optionally be substituted with one or more substituents such as alkyl or alkoxy groups.

Exemplary fluorene and fluorene analogue repeat units include repeat units of formula (VII):

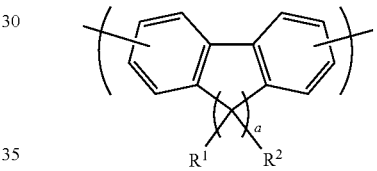

wherein $R^1$ and $R^2$ are independently in each occurrence H or a substituent, a is at least 1, optionally 1, 2 or 3, and wherein $R^1$ and $R^2$ attached to the same C atom may be linked to form a ring.

Exemplary repeat units of formula (VII) include units of formula (VIIa) wherein a is 1, and repeat units of formula (VIIb) wherein a is 2:

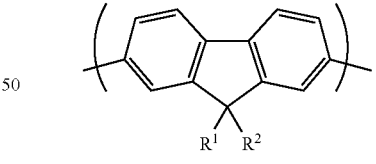

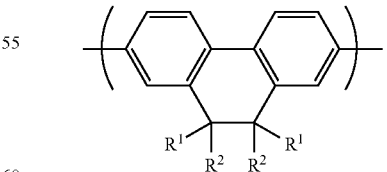

$R^1$ and $R^2$ are optionally selected from the group consisting of hydrogen; optionally substituted $Ar^3$ or a linear or branched chain of $Ar^3$ groups, wherein $Ar^3$ is as described above with reference to formula (VI); optionally substituted alkyl, for example $C_{1-20}$ alkyl, wherein one or more non-adjacent C atoms of the alkyl group may be replaced with O, S, substituted N, C=O and —COO—; and a crosslinking unit that may be either directly bound to the fluorene unit or spaced from the fluorene unit by a spacer group as described above.

In the case where $R^1$ or $R^2$ contains a crosslinkable unit, the crosslinkable unit may or may not be a unit of formula (I). If the crosslinkable unit is not a unit of formula (I) then the crosslinkable unit may be a unit that reacts with a unit of formula (I) that may be provided as a substituent of another repeat unit of the polymer, or in a compound mixed with the polymer.

In the case where $R^1$ or $R^2$ comprises alkyl, optional substituents of the alkyl group include F, CN, nitro, and aryl or heteroaryl optionally substituted with one or more groups $R^4$ wherein $R^4$ is as described above.

In the case where $R^1$ or $R^2$ comprises aryl or heteroaryl, each aryl or heteroaryl group may independently be substituted, and the aryl or heteroaryl group is preferably phenyl. Preferred optional substituents for the aryl or heteroaryl groups include one or more substituents $R^3$ as described above with reference to formula (VI).

Optional substituents for the fluorene unit, other than substituents $R^1$ and $R^2$, are preferably selected from the group consisting of alkyl wherein one or more non-adjacent C atoms may be replaced with O, S, substituted N, C=O and —COO—, optionally substituted aryl, optionally substituted heteroaryl, fluorine, cyano and nitro.

Where present, substituted N in repeat units of formula (VII) may independently in each occurrence be $NR^5$ or $NR^6$.

In one preferred arrangement, at least one of $R^1$ and $R^2$ comprises an optionally substituted $C_1$-$C_{20}$ alkyl or an optionally substituted aryl group, in particular phenyl substituted with one or more $C_{1-20}$ alkyl groups.

Exemplary phenylene repeat units include repeat units of formula (VIII):

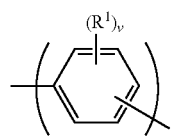

(VIII)

wherein $R^1$ is as described above with reference to formula (VII); v is 0, 1, 2, 3 or 4; each $R^1$ is the same or different in the case where v is 2, 3 or 4; and adjacent groups $R^1$ may be linked to form a ring. Optionally, v is 1 or 2. Optionally, $R^1$ in each occurrence is an optionally substituted $C_1$-$C_{20}$ alkyl. Optionally, the unit of formula (VIII) is 1,4-linked.

In one preferred arrangement, the repeat unit of formula (VIII) is 1,4-linked and a substituent $R^1$ is present in the 2-position and optionally also in the 5-position.

In the case wherein one or more substituents $R^1$ contain a crosslinkable unit, the crosslinkable unit may be either bound directly to the phenyl group of formula (VIII) or spaced apart therefrom by a spacer group, for example a spacer group as described above. The crosslinkable unit may or may not be a unit of formula (I). If the crosslinkable unit is not a unit of formula (I) then the crosslinkable unit may be a unit that reacts with a unit of formula (I) that may be provided as a substituent of another repeat unit of the polymer, or in a compound mixed with the polymer.

(iii) Triplet quenching repeat units—a triplet quenching repeat unit is a unit which, when introduced into a polymer, provides a reduced triplet energy level of the polymer as compared to the polymer in which the triplet-quenching repeat unit is absent. The triplet quenching repeat unit may provide a path for triplet excitons to decay non-radiatively, thus reducing the probability of triplet-triplet interactions that may be detrimental to device performance.

A exemplary triplet quenching repeat unit has formula (IX):

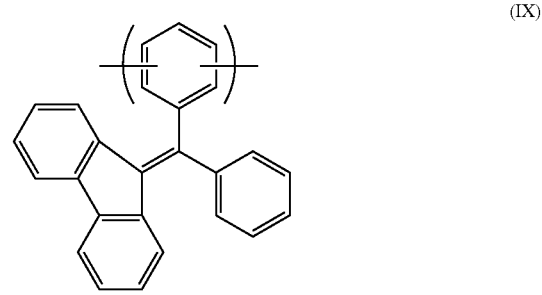

(IX)

The repeat unit of formula (IX) may be substituted or unsubstituted. Exemplary substituents include one or more substituents $R^3$ as described above with reference to formula (VI), preferably one or more $C_{1-20}$ alkyl groups.

(iv) An exemplary triazine repeat unit of a host polymer has formula (XIV):

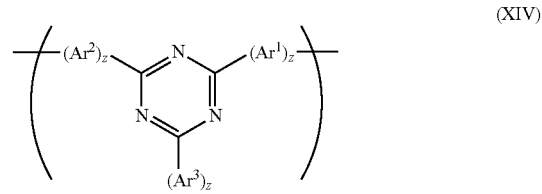

(XIV)

wherein $Ar^1$, $Ar^2$ and $Ar^3$ are as described with reference to formula (VI) above, and may each independently be substituted with one or more substituents described with reference to $Ar^1$, $Ar^2$ and $Ar^3$, and z in each occurrence is independently at least 1, optionally 1, 2 or 3. Preferably, $Ar^1$ and $Ar^2$ and $Ar^3$ of formula (XIV) are each phenyl, each phenyl being optionally and independently substituted with one or more $C_{1-20}$ alkyl groups.

$Ar^3$ of formula (XIV) is preferably phenyl, and is optionally substituted with one or more $C_{1-20}$ alkyl groups or a crosslinkable unit. The crosslinkable unit may or may not be a unit of formula (I) bound directly to $Ar^3$ or spaced apart from $Ar^3$ by a spacer group, for example a spacer group as described above. If the crosslinkable unit is not a unit of formula (I) then the crosslinkable unit may be a unit that reacts with a unit of formula (I) that may be provided as a substituent of another repeat unit of the polymer, or in a compound mixed with the polymer.

The polymer may comprise repeat units that block or reduce conjugation along the polymer chain and thereby increase the polymer bandgap. For example, the polymer may comprise units that are twisted out of the plane of the polymer backbone, reducing conjugation along the polymer backbone, or units that do not provide any conjugation path along the polymer backbone. Exemplary repeat units that reduce conjugation along the polymer backbone are substituted or unsubstituted 1,3-substituted phenylene repeat units of formula (VIII) and 1,4-phenylene repeat units of formula (VIII) substituted with a $C_{1-20}$ alkyl group in the 2- and/or 5-position.

Polymer Synthesis

Preferred methods for preparation of conjugated polymers, such as polymers comprising one or more of repeat units of formulae (IIIa), (IIIb), (VI), (VII), (VIII), (IX) and (XIV) as described above, comprise a "metal insertion" wherein the metal atom of a metal complex catalyst is inserted between an aryl or heteroaryl group and a leaving group of a monomer. Exemplary metal insertion methods are Suzuki polymerisation as described in, for example, WO 00/53656 and Yamamoto polymerisation as described in, for example, T. Yamamoto, "Electrically Conducting And Thermally Stable π-Conjugated Poly(arylene)s Prepared by Organometallic Processes", Progress in Polymer Science 1993, 17, 1153-1205. In the case of Yamamoto polymerisation, a nickel complex catalyst is used; in the case of Suzuki polymerisation, a palladium complex catalyst is used.

For example, in the synthesis of a linear polymer by Yamamoto polymerisation, a monomer having two reactive halogen groups is used. Similarly, according to the method of Suzuki polymerisation, at least one reactive group is a boron derivative group such as a boronic acid or boronic ester and the other reactive group is a halogen. Preferred halogens are chlorine, bromine and iodine, most preferably bromine.

It will therefore be appreciated that repeat units illustrated throughout this application may be derived from a monomer carrying suitable leaving groups. Likewise, an end group or side group may be bound to the polymer by reaction of a suitable leaving group.

Suzuki polymerisation may be used to prepare regioregular, block and random copolymers. In particular, homopolymers or random copolymers may be prepared when one reactive group is a halogen and the other reactive group is a boron derivative group. Alternatively, block or regioregular copolymers may be prepared when both reactive groups of a first monomer are boron and both reactive groups of a second monomer are halogen.

As alternatives to halides, other leaving groups capable of participating in metal insertion include sulfonic acids and sulfonic acid esters such as tosylate, mesylate and triflate.

Charge Transporting and Charge Blocking Layers

A hole transporting layer may be provided between the anode and the light-emitting layer or layers. Likewise, an electron transporting layer may be provided between the cathode and the light-emitting layer or layers.

Similarly, an electron blocking layer may be provided between the anode and the light-emitting layer and a hole blocking layer may be provided between the cathode and the light-emitting layer. Transporting and blocking layers may be used in combination. Depending on its HOMO and LUMO levels, a single layer may both transport one of holes and electrons and block the other of holes and electrons.

A charge-transporting layer or charge-blocking layer may be crosslinked, particularly if a layer overlying that charge-transporting or charge-blocking layer is deposited from a solution. The crosslinkable group used for this crosslinking may be a crosslinkable group comprising a unit of formula (I).

If present, a hole transporting layer located between the anode and the light-emitting layers preferably has a HOMO level of less than or equal to 5.5 eV, more preferably around 4.8-5.5 eV as measured by photoelectron spectroscopy. The HOMO level of the hole transport layer may be selected so as to be within 0.2 eV, optionally within 0.1 eV, of an adjacent layer (such as a light-emitting layer) in order to provide a small barrier to hole transport between these layers.

If present, an electron transporting layer located between the light-emitting layers and cathode preferably has a LUMO level of around 3-3.5 eV as measured by square wave cyclic voltammetry. For example, a layer of a silicon monoxide or silicon dioxide or other thin dielectric layer having thickness in the range of 0.2-2 nm may be provided between the light-emitting layer nearest the cathode and the cathode. HOMO and LUMO levels may be measured using cyclic voltammetry.

A hole transporting layer may contain a hole-transporting (hetero)arylamine, such as a homopolymer or copolymer comprising hole transporting repeat units of formula (VI). Exemplary copolymers comprise repeat units of formula (VI) and optionally substituted (hetero)arylene co-repeat units, such as phenyl, fluorene or indenofluorene repeat units as described above, wherein each of said (hetero)arylene repeat units may optionally be substituted with one or more substituents such as alkyl or alkoxy groups. Specific co-repeat units include fluorene repeat units of formula (VII) and optionally substituted phenylene repeat units of formula (VIII) as described above.

An electron transporting layer may contain a polymer comprising a chain of optionally substituted arylene repeat units, such as a chain of fluorene repeat units.

Light-Emitting Layers

Suitable light-emitting materials for use in the light-emitting layer or layers of an OLED include small molecule, polymeric and dendrimeric materials, and compositions thereof. Suitable light-emitting polymers include conjugated polymers, for example substituted or unsubstituted poly(arylene vinylenes) such as poly(p-phenylene vinylenes) and substituted or unsubstituted polyarylenes such as: polyfluorenes, particularly 2,7-linked 9,9 dialkyl polyfluorenes or 2,7-linked 9,9 diaryl polyfluorenes; polyspirofluorenes, particularly 2,7-linked poly-9,9-spirofluorene; polyindenofluorenes, particularly 2,7-linked polyindenofluorenes; polyphenylenes, particularly alkyl or alkoxy substituted poly-1,4-phenylene. Such polymers as disclosed in, for example, Adv. Mater. 2000 12(23) 1737-1750 and references therein.

Polymers for use as light-emitting materials in devices according to the present invention may comprise a repeat unit selected from substituted or unsubstituted amine repeat units of formula (VI) and/or substituted or unsubstituted arylene or heteroarylene repeat units as described above, in particular fluorene repeat units of formula (VII) and/or phenylene repeat units of formula (VIII) described above. The light-emitting layer may be crosslinked in the case where the light-emitting layer includes a polymer, for example by crosslinking of a crosslinkable unit of formula (I) provided in the light-emitting layer.

The light-emitting layer may consist of a light-emitting material alone, or may comprise this material in combination with one or more further materials. In particular, the light-emitting material may be blended with hole and/or electron transporting materials or alternatively may be covalently bound to hole and/or electron transporting materials as disclosed in for example, WO 99/48160.

Light-emitting copolymers may comprise a light-emitting region and at least one of a hole transporting region and an electron transporting region as disclosed in, for example, WO 00/55927 and U.S. Pat. No. 6,353,083. If only one of a hole transporting region and electron transporting region is provided then the electroluminescent region may also provide the other of hole transport and electron transport functionality—for example, an amine unit of formula (VI) as described above may provide both hole transport and light-emission functionality. A light-emitting copolymer comprising light-emitting repeat units and one or both of a hole transporting repeat units and electron transporting repeat units may provide said units in a polymer main-chain, as per U.S. Pat. No. 6,353,083, or in polymer side-groups pendant from the polymer backbone.

Suitable light-emitting materials may emit in the UV, visible and/or infra-red region of the electromagnetic spectrum. The OLED may contain one or more of red, green and blue light-emitting materials.

A blue light-emitting material may have photoluminescent spectrum with a peak wavelength in the range of less than or equal to 480 nm, such as in the range of 400-480 nm.

A green light-emitting material may have photoluminescent spectrum with a peak wavelength in the range of above 480 nm-560 nm.

A red light-emitting material may have photoluminescent spectrum with a peak wavelength in the range of above 560 nm-630 nm.

More than one light-emitting material may be used. For example, red, green and blue light-emitting dopants may be used to obtain white light emission.

The light emitting layer may comprise a host material and at least one light-emitting dopant. The host material may be a material as described above that would, in the absence of a dopant, emit light itself. When a host material and dopant are used in a device, the dopant alone may emit light. Alternatively, the host material and one or more dopants may emit light. White light may be generated by emission from multiple light sources, such as emission from both the host and one or more dopants or emission from multiple dopants.

In the case of a fluorescent light-emitting dopant the singlet excited state energy level ($S_1$) of the host material should be higher than that of the fluorescent light-emitting dopant in order that singlet excitons may be transferred from the host material to the fluorescent light-emitting dopant. Likewise, in the case of a phosphorescent light-emitting dopant the triplet excited state energy level ($T_1$) of the host material should be higher than that of the phosphorescent light-emitting dopant in order that triplet excitons may be transferred from the host material to the fluorescent light-emitting dopant.

Exemplary phosphorescent light-emitting dopants include metal complexes comprising substituted or unsubstituted complexes of formula (X):

$$ML^1_qL^2_rL^3_s \quad (X)$$

wherein M is a metal; each of $L^1$, $L^2$ and $L^3$ is a coordinating group; q is an integer; r and s are each independently 0 or an integer; and the sum of $(a \cdot q)+(b \cdot r)+(c \cdot s)$ is equal to the number of coordination sites available on M, wherein a is the number of coordination sites on $L^1$, b is the number of coordination sites on $L^2$ and c is the number of coordination sites on $L^3$.

Heavy elements M induce strong spin-orbit coupling to allow rapid intersystem crossing and emission from triplet or higher states (phosphorescence). Suitable heavy metals M include d-block metals, in particular those in rows 2 and 3 i.e. elements 39 to 48 and 72 to 80, in particular ruthenium, rhodium, palladium, rhenium, osmium, iridium, platinum and gold. Iridium are particularly preferred.

Exemplary ligands $L^1$, $L^2$ and $L^3$ include carbon or nitrogen donors such as porphyrin or bidentate ligands of formula (XI):

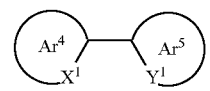

(XI)

wherein $Ar^4$ and $Ar^5$ may be the same or different and are independently selected from substituted or unsubstituted aryl or heteroaryl; $X^1$ and $Y^1$ may be the same or different and are independently selected from carbon or nitrogen; and $Ar^4$ and $Ar^5$ may be fused together. Ligands wherein $X^1$ is carbon and $Y^1$ is nitrogen are particularly preferred.

Examples of bidentate ligands are illustrated below:

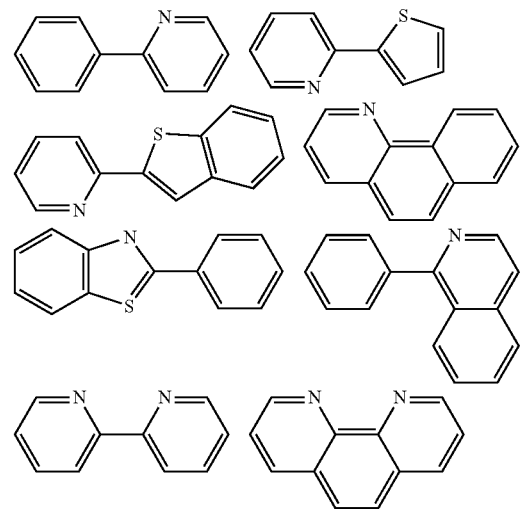

Each of $Ar^4$ and $Ar^y$ may carry one or more substituents. Two or more of these substituents may be linked to form a ring, for example an aromatic ring.

Other ligands suitable for use with d-block elements include diketonates, in particular acetylacetonate (acac); triarylphosphines and pyridine, each of which may be substituted.

Exemplary substituents include groups $R^3$ groups $R^3$ as described above with reference to Formula (VI). Particularly preferred substituents include fluorine or trifluoromethyl which may be used to blue-shift the emission of the complex, for example as disclosed in WO 02/45466, WO 02/44189, US 2002-117662 and US 2002-182441; alkyl or alkoxy groups, for example $C_{1-20}$ alkyl or alkoxy, which may be as disclosed in JP 2002-324679; carbazole which may be used to assist hole transport to the complex when used as an emissive material, for example as disclosed in WO 02/81448; bromine, chlorine or iodine which can serve to functionalise the ligand for attachment of further groups, for example as disclosed in WO 02/68435 and EP 1245659; and dendrons which may be used to obtain or enhance solution processability of the metal complex, for example as disclosed in WO 02/66552.

A light-emitting dendrimer typically comprises a light-emitting core bound to one or more dendrons, wherein each dendron comprises a branching point and two or more dendritic branches. Preferably, the dendron is at least partially conjugated, and at least one of the branching points and dendritic branches comprises an aryl or heteroaryl group, for example a phenyl group. In one arrangement, the branching point group and the branching groups are all phenyl, and each phenyl may independently be substituted with one or more substituents, for example alkyl or alkoxy.

A dendron may have optionally substituted formula (XII)

(XII)

wherein BP represents a branching point for attachment to a core and $G_1$ represents first generation branching groups.

The dendron may be a first, second, third or higher generation dendron. $G_1$ may be substituted with two or more second generation branching groups $G_2$, and so on, as in optionally substituted formula (XIIa):

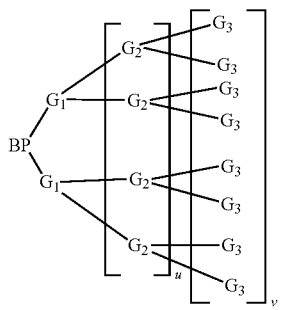
(XIIa)

wherein u is 0 or 1; v is 0 if u is 0 or may be 0 or 1 if u is 1; BP represents a branching point for attachment to a core and $G_1$, $G_2$ and $G_3$ represent first, second and third generation dendron branching groups.

BP and/or any group G may be substituted with one or more substituents, for example one or more $C_{1-20}$ alkyl or alkoxy groups.

Where used, a light-emitting dopant may be present in an amount of about 0.05 mol % up to about 20 mol %, optionally about 0.1-10 mol % relative to their host material.

The light-emitting dopant may be physically mixed with the host material or it may be chemically bound to the host material in the same manner described above with respect to binding of the light-emitting dopant to the charge transporting material.

More than one light-emitting layer may be present. Multiple light-emitting layers may together produce white light.

The light-emitting layer may be patterned or unpatterned. A device comprising an unpatterned layer may be used an illumination source, for example. A white light emitting device is particularly suitable for this purpose. A device comprising a patterned layer may be, for example, an active matrix display or a passive matrix display. In the case of an active matrix display, a patterned electroluminescent layer is typically used in combination with a patterned anode layer and an unpatterned cathode. In the case of a passive matrix display, the anode layer is formed of parallel stripes of anode material, and parallel stripes of electroluminescent material and cathode material arranged perpendicular to the anode material wherein the stripes of electroluminescent material and cathode material are typically separated by stripes of insulating material ("cathode separators") formed by photolithography.

Hole Injection Layers

A conductive hole injection layer, which may be formed from a conductive organic or inorganic material, may be provided between the anode and the light-emitting layer or layers to assist hole injection from the anode into the layer or layers of semiconducting polymer. A hole transporting layer may be used in combination with a hole injection layer.

Examples of doped organic hole injection materials include optionally substituted, doped poly(ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. No. 5,723,873 and U.S. Pat. No. 5,798,170; and optionally substituted polythiophene or poly(thienothiophene). Examples of conductive inorganic materials include transition metal oxides such as VOx MoOx and RuOx as disclosed in Journal of Physics D: Applied Physics (1996), 29(11), 2750-2753.

Cathode

The cathode is selected from materials that have a workfunction allowing injection of electrons into the light-emitting layer or layers. Other factors influence the selection of the cathode such as the possibility of adverse interactions between the cathode and the light-emitting materials. The cathode may consist of a single material such as a layer of aluminium. Alternatively, it may comprise a plurality of metals, for example a bilayer of a low workfunction material and a high workfunction material such as calcium and aluminium as disclosed in WO 98/10621. The cathode may contain a layer containing elemental barium as disclosed in WO 98/57381, Appl. Phys. Lett. 2002, 81(4), 634 and WO 02/84759, for example a layer of barium capped with one or more further conductive layers such as aluminium and/or silver. The cathode may contain a thin layer of a metal compound, in particular an oxide or fluoride of an alkali or alkali earth metal, between the light-emitting layer(s) of the OLED and one or more conductive layers of the cathode, for example one or more metal layers. Such metal compounds may assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a workfunction of less than 3.5 eV, more preferably less than 3.2 eV, most preferably less than 3 eV. Work functions of metals can be found in, for example, Michaelson, J. Appl. Phys. 48(11), 4729, 1977.

The cathode may directly contact a light-emitting layer, or may be spaced apart from the light-emitting layer(s) by one or more further layers, for example a semiconducting electron-transport layer.

The cathode may be opaque or transparent. Transparent cathodes are particularly advantageous for active matrix devices because emission through a transparent anode in such devices is at least partially blocked by drive circuitry located underneath the emissive pixels. A transparent cathode comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Encapsulation

Organic optoelectronic devices tend to be sensitive to moisture and oxygen. Accordingly, the substrate 1 preferably has good barrier properties for prevention of ingress of moisture and oxygen into the device. The substrate is may be glass, however alternative substrates may be used, in particular where flexibility of the device is desirable. For example, the substrate may comprise a plastic either alone or in combination with other substrate layers, such as a substrate of alternating plastic and ceramic layers or a laminate of thin glass and plastic such as is disclosed in EP 0949850.

The device may be encapsulated with an encapsulant (not shown) to prevent ingress of moisture and oxygen. Suitable encapsulants include a sheet of glass, films having suitable barrier properties such as silicon dioxide, silicon monoxide, silicon nitride or alternating stacks of polymer and dielectric as disclosed in, for example, WO 01/81649 or an airtight container as disclosed in, for example, WO 01/19142. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Solution Processing

Suitable solvents for forming solution processable formulations of the composition may be selected from common organic solvents, such as mono- or poly-alkylbenzenes such as toluene and xylene.

Exemplary solution deposition techniques including printing and coating techniques such spin-coating, dip-coating, roll-to-roll coating or roll-to-roll printing, doctor blade coating, slot die coating, gravure printing, screen printing and inkjet printing.

Coating methods, such as those described above, are particularly suitable for devices wherein patterning of the light-emitting layer or layers is unnecessary—for example for lighting applications or simple monochrome segmented displays.

Printing is particularly suitable for high information content displays, in particular full colour displays. A device may be inkjet printed by providing a patterned layer over the first electrode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

EXAMPLES

Monomer Example 1

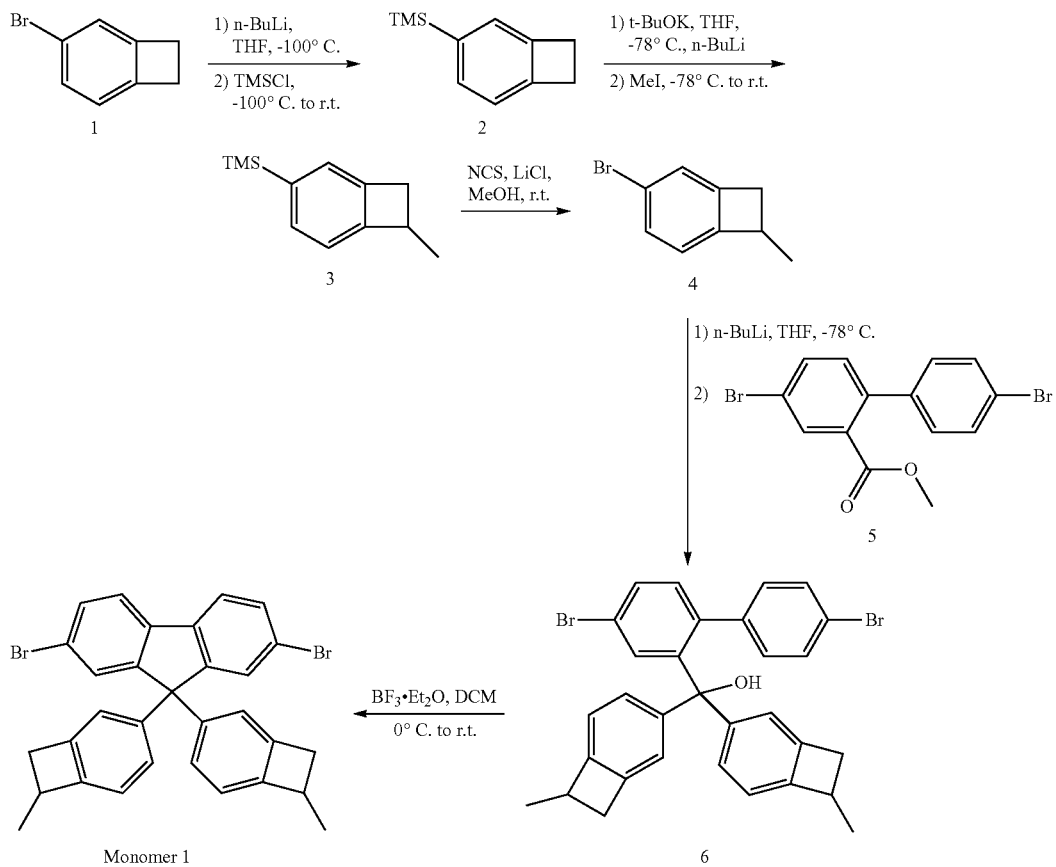

Monomer 1

3-Trimethylsilylbicyclo[4.2.0]octa-1,3,5-triene (2)

To a solution of 3-bromobicyclo[4.2.0]octa-1,3,5-triene (1) (50.0 g, 0.27 mol) in THF (500 ml) at −100° C., was added n-BuLi (2.5M, 115 ml, 0.29 mol) drop wise such as to maintain the internal temperature below −95° C. The mixture was stirred for 3 hrs at −100° C. and trimethyl silyl chloride (36.7 ml, 0.29 mol) was added drop wise to it such as to maintain the internal temperature below −95° C. The mixture was allowed to warm up to room temperature over night.

The reaction mixture was cooled to 0° C., quenched with $H_2O$ (200 ml) and concentrated under reduced pressure. The residue was extracted with hexane (3×200 ml), the combined organic extracts were washed with $H_2O$ (3×200 ml), dried over $MgSO_4$ and concentrated under reduce pressure to yield 3-trimethylsilylbicyclo[4.2.0]octa-1,3,5-triene (2) as an orange oil (56 g, GC-MS: $M^+$=176), which was used without further purification in the next step.

7-Methyl-3-trimethylsilylbicyclo[4.2.0]octa-1,3,5-triene (3)

To a solution of t-BuOK (45.9 g, 0.41 mol) in THF (1000 ml) at −74° C. was added 3-trimethylsilylbicyclo[4.2.0]octa-1,3,5-triene (2) (48.2 g, 0.27 mol), followed by n-BuLi (164 ml, 0.41 mol) and the resulting solution was stirred for 1 hr at −74° C. Methyl iodide (50.2 ml, 0.30 mol) was then added drop wise to the solution and the reaction mixture was allowed to warm up to room temperature overnight.

The reaction mixture was cooled to 0° C., quenched with an aqueous solution of $NH_4Cl$ (400 ml, 10% w/v) and concentrated under reduced pressure. The residue was extracted with hexane (3×200 ml), the combined organic extracts were washed with $H_2O$ (3×200 ml), dried over $MgSO_4$ and concentrated under reduced pressure to give an orange oil. The oil was filtered through a plug (silica, hexane) to yield 48.1 g of 7-methyl-3-trimethylsilylbicyclo[4.2.0]octa-1,3,5-triene (3) as a colourless oil (48.1 g, GC-MS: $M^+$=190, 92.8% yield, isolated as a mixture of isomers).

3-Bromo-7-methyl-bicyclo[4.2.0]octa-1,3,5-triene (4)

To a solution of 7-methyl-3-trimethylsilylbicyclo[4.2.0]octa-1,3,5-triene (3) (48.1 g, 0.25 mol) in MeOH (1000 ml) at 25° C., was added N-chlorosuccinimide (37.1 g, 0.28 mol), followed by lithium bromide (24.1 g, 0.28 mol) and the reaction mixture was allowed to stir at this temperature for 2 hrs. It was then quenched with $H_2O$ (200 ml), and concentrated under reduced pressure. The residue was extracted with hexane (200 ml×4), the combined organic extracts were washed with H2O (3×200 ml), dried over $MgSO_4$ and concentrated under reduce pressure to give a pale yellow oil. The oil was purified by column chromatography (silica, hexane) to give the desired product 3-bromo-7-methyl-bicyclo[4.2.0]octa-1,3,5-triene (4) as a colourless oil (42.6 g, GC-MS: $M^+$=196, $M^-$=198, isolated as a mixture of isomers).

$^1$H NMR (600 MHz, $CDCl_3$): δ=1.37 (d, J=7.1 Hz, 3H), 2.68 (d, J=14.2 Hz, 1H), 3.36 (dd, J=14.1 Hz, 5.2 Hz, 1H), 3.49 (m, 1H), 6.92 (d, J=7.7 Hz, 1H), 7.20 (s, 1H), 7.33 (d, J=7.7 Hz, 1H).

1-(4,4'-Dibromobiphenyl-2-yl)-1,1-bis(7"-methyl-bicyclo[4.2.0]octa-1",3",5"-triene-3"-yl)methanol (6)

To a solution of 3-bromo-7-methyl-bicyclo[4.2.0]octa-1,3,5-triene (4) (42.6 g, 0.21 mol) in THF (365 ml) at −74° C. was added n-BuLi (2.5M, 82.6 ml, 0.21 mol) drop wise and the mixture was stirred at this temperature for 3 hrs. 4-4'-Dibromo-biphenyl-2-carboxylic acid methyl ester (5) (34.4 g, 0.09 mol) in solution in THF (60 ml) was added drop wise and the mixture was allowed to warm up to room temperature over night.

The reaction mixture was cooled to 0° C., quenched with HCl (2M, 90 ml), concentrated under reduced pressure and the residue was extracted with hexane (3×200 ml). The combined organic extracts were washed with $H_2O$ (3×200 ml), dried over $MgSO_4$ and concentrated under reduce pressure to give a yellow oil. The oil was purified by column chromatography (silica, 45% toluene:hexane) to give the desired product 1-(4,4'-dibromobiphenyl-2-yl)-1,1-bis(7"-methyl-bicyclo[4.2.0]octa-1",3",5"-triene-3"-yl)methanol (6) as a of white foam (24.1 g, 45.1% yield).

2,7-Dibromo-9,9-bis(7'-methyl-bicyclo[4.2.0]octa-1',3',5'-triene-3'-yl)fluorene (Monomer 1)

To a solution of 1-(4,4'-dibromobiphenyl-2-yl)-1,1-bis(7"-methyl-bicyclo[4.2.0]octa-1",3",5"-triene-3"-yl)methanol (6) (24.1 g, 0.04 mol) in DCM (80 ml) at −5° C. was added boron trifluoride diethyl etherate (25.8 ml, 0.21 mol) drop wise and the mixture was allowed to warm room temperature over night. The reaction mixture was poured into a mixture of ice/water (200 ml) and stirred for 30 min. The organic phase was separated and stirred over an aqueous solution of potassium phosphate tribasic (80 ml, 10% w/v) for 1 hr. The organic phase was separated, washed with $H_2O$ (3×80 ml), dried over $MgSO_4$ and concentrated under reduce pressure to give a yellow solid. The solid was purified by column chromatography (silica, 96% hexane: DCM) and then 1 g was further purified by preparative HPLC to give 2,7-Dibromo-9,9-bis(7'-methyl-bicyclo[4.2.0]octa-1',3',5'-triene-3'-yl)fluorene (Monomer 1) as a white solid (0.3 g, 95.98% pure by HPLC, isolated as a mixture of isomers).

$^1$H NMR (600 MHz, $CDCl_3$): δ=1.36 (d, J=7.1 Hz, 6H), 2.62 (dd, J=14.1 Hz, 1.7 Hz, 2H), 3.28 (dd, J=14.1 Hz, 5.3 Hz, 2H), 3.49 (m, 2H), 6.81 (s, 2H), 6.91 (d, J=7.7 Hz, 2H), 6.99 (d, J=7.7 Hz, 2H), 7.45 (d, J=8.1 Hz, 2H), 7.50 (s, 2H), 7.56 (d, J=8.1 Hz, 2H).

Monomer Example 2

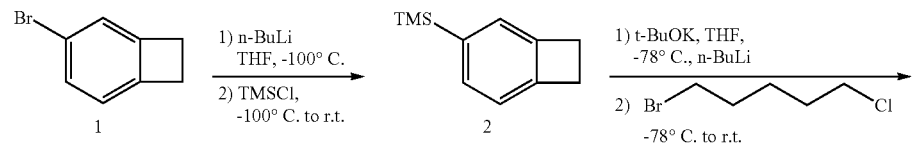

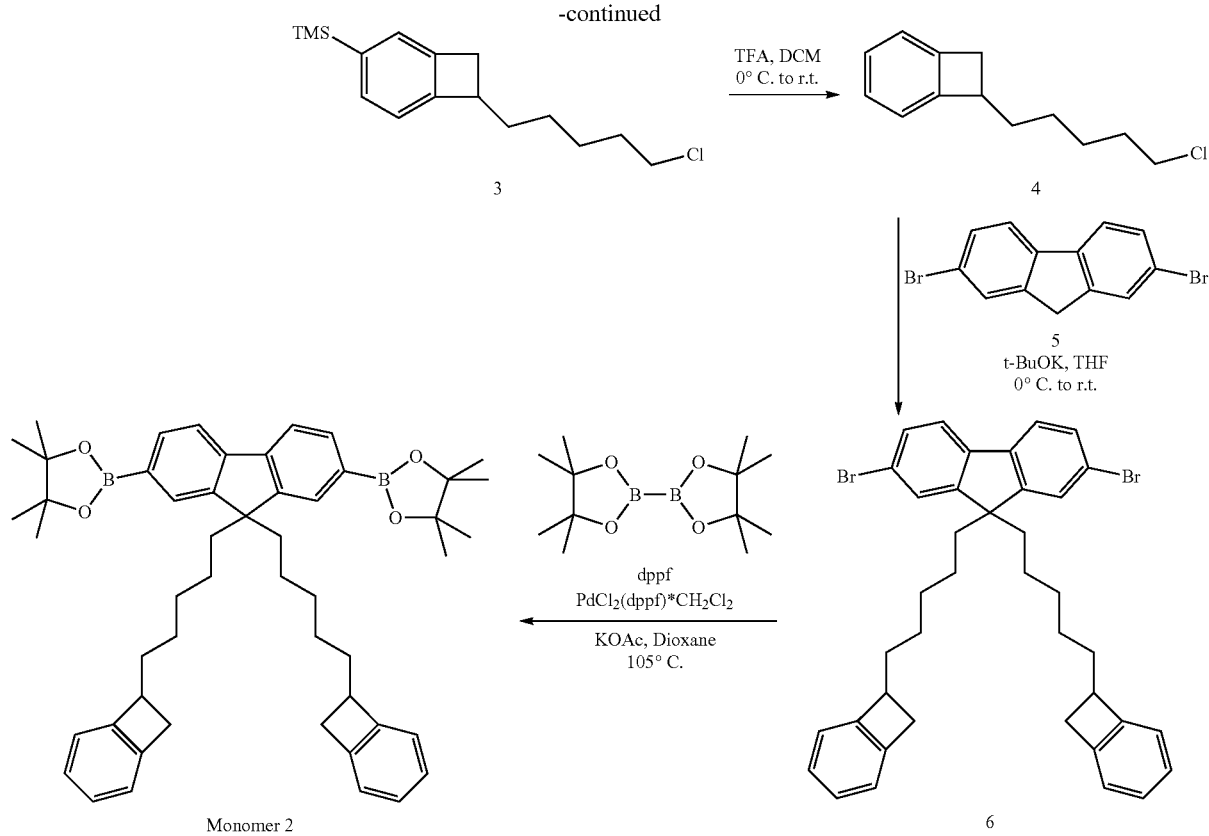

Monomer 2

3-Trimethylsilylbicyclo[4.2.0]octa-1,3,5-triene (2)

To a solution of 3-bromobicyclo[4.2.0]octa-1,3,5-triene (1) (50.8 g, 0.278 mol) in THF (500 ml) at −100° C., was added n-BuLi (2.5M, 117 ml, 0.291 mol) drop wise such as to maintain the internal temperature below −95° C. The mixture was stirred for 3 hrs at −100° C. and trimethyl silyl chloride (37.2 ml, 0.291 mol) was added drop wise so as to maintain the internal temperature below −95° C. The mixture was allowed to warm up to room temperature over night.

The reaction mixture was cooled to 0° C., quenched with $H_2O$ (200 ml) and concentrated under reduced pressure. The residue was extracted with hexane (3×200 ml), the combined organic extracts were washed with $H_2O$ (3×200 ml), dried over $MgSO_4$ and concentrated under reduce pressure to yield 3-trimethylsilylbicyclo[4.2.0]octa-1,3,5-triene (2) as a colourless oil (53 g).

GC-MS: $M^+$=176, $^1H$ NMR (600 MHz, $CDCl_3$): δ=0.26 (s, 9H), 3.19 (m, 4H), 7.07 (d, J=7.3 Hz, 1H), 7.24 (s, 1H), 7.38 (d, J=7.3 Hz, 1H).

7-(5'-Chloro-pentyl)-3-trimethylsilylbicyclo[4.2.0]octa-1,3,5-triene (3)

To a solution of potassium tert-butoxide (45.7 g, 0.408 mol) in THF (200 ml) at −74° C. was added drop wise 3-trimethylsilylbicyclo[4.2.0]octa-1,3,5-triene (2) (47.9 g, 0.272 mol), followed by n-BuLi (2.5M, 163 ml, 0.408 mol) and the resulting solution was allowed to warm up to room temperature. It was then added drop wise to a solution of 1-bromo-5-chloropentane (37.6 ml, 0.285 mol) in THF (440 ml) at −74° C. The reaction mixture was allowed to warm up to room temperature overnight.

The reaction mixture was cooled to 0° C., quenched with $H_2O$ (250 ml) and concentrated under reduced pressure. The residue was extracted with hexane (3×200 ml), the combined organic extracts were washed with $H_2O$ (3×200 ml), dried over $MgSO_4$ and concentrated under reduce pressure to give an orange liquid. Purification by column chromatography (silica, 10% dichloromethane:hexane) to yield 48.1 g of 7-(5-chloro-pentyl)-3-trimethylsilylbicyclo[4.2.0]octa-1,3,5-triene (3) as a colourless liquid (48.1 g, 68% yield, isolated as a mixture of isomers).

GC-MS: $M^+$=280

7-(5'Chloro-pentyl)-bicyclo[4.2.0]octa-1,3,5-triene (4)

To a solution of 7-(5'-chloro-pentyl)-3-trimethylsilylbicyclo[4.2.0]octa-1,3,5-triene (3) (51.7 g, 0.184 mol) in dichloromethane (220 ml) at 0° C., was added drop wise trifluoroacetic acid (18.0 ml, 0.242 mol) and the reaction mixture was allowed to stir at room temperature for 4 hrs. The reaction mixture was cooled down to 0° C. and quenched with $H_2O$ (200 ml). The aqueous phase was extracted with dichloromethane (200 ml×2), the combined organic extracts were washed with $H_2O$ (4×200 ml), dried over $MgSO_4$ and concentrated under reduce pressure to give a yellow liquid. The liquid was purified by column chromatography (silica, 10% dichloromethane:hexane) to give the desired product 7-(5-chloro-pentyl)-bicyclo[4.2.0]octa-1,3,5-triene (4) as a colourless liquid (27.1 g, 70% yield).

GC-MS: $M^+$=208, $^1H$ NMR (600 MHz, $CDCl_3$): δ=1.52 (m, 4H), 1.70 (m, 2H), 1.82 (m, 2H), 3.49 (m, 1H), 2.73 (dd,

J=13.9 Hz, J=2.4 Hz, 1H), 3.32 (dd, J=13.9 Hz, J=5.2 Hz, 1H), 3.46 (m, 1H), 3.56 (t, J=6.7 Hz, 2H), 7.07 (m, 2H), 7.19 (m, 2H).

2,7-Dibromo-9,9-bis(5'-pentyl-bicyclo[4.2.0]octa-1",3",5"-triene-7"-yl)fluorene (6)

To a solution of 2,7-dibromofluorene (5) (19.1 g, 0.059 mol) in THF (270 ml) was added potassium tert-butoxide (19.9 g, 0.177 mol), the mixture was stirred for 1 hr at room temperature and 7-(5'-chloro-pentyl)-bicyclo[4.2.0]octa-1,3,5-triene (4) (27.1 g, 0.130 mol). The reaction mixture was at room temperature over night.

The reaction mixture was filtered (aluminum oxide, 50% hexane:dichloromethane) and the filtrate was concentrated under reduced pressure. The residue was subjected to column chromatography (silica, gradient of hexane:dichloromethane) to give a colourless oil. The oil was dissolved in dichloromethane (200 ml), sulphuric acid (95-97%, 20 ml) was added and the mixture was stirred for 30 min. The organic extract was washed with sulphuric acid (95-97%, 20 ml×2), sodium acetate (10% wt/v, 100 ml), dried over $MgSO_4$ and concentrated under reduce pressure. The residue was filtered through a plug (silica, 30% dichloromethane: hexane) and concentrated under reduce pressure to give the desired product 2,7-dibromo-9,9-bis(5'-pentyl-bicyclo[4.2.0]octa-1",3",5"-triene-7"-yl)fluorene (6) as a colourless oil (14.0 g, 36% yield, purity: 95.4% by HPLC).

$^1$H NMR (600 MHz, $CDCl_3$): δ=0.61 (m, 4H), 1.14 (m, 4H), 1.28 (m, 4H), 1.52 (m, 4H), 1.94 (m, 4H), 2.64 (dd, J=13.9 Hz, 2.2 Hz, 2H), 3.24 (dd, J=13.9 Hz, 5.2 Hz, 2H), 3.33 (m, 2H), 7.01 (d, J=6.5 Hz, 2H), 7.03 (d, J=6.7 Hz, 2H), 7.15 (m, 4H), 7.45 (m, 4H), 7.53 (m, 2H).

2,7-Boronic acid pinacol ester-9,9-bis(5'-pentyl-bicyclo[4.2.0]octa-1",3",5"-triene-7"-yl)fluorene (Monomer 2)

A solution of 2,7-dibromo-9,9-bis(5'-pentyl-bicyclo[4.2.0]octa-1",3",5"-triene-7"-yl)fluorene (6) (14.0 g, 0.021 mol) in 1,4-dioxane (140 ml) was degassed for 1 hr, 1,1'-bis(diphenylphosphino)ferrocene (0.174 g, 0.0003 mol) and 1,1'-bis(diphenylphosphino)ferrocene dichloro palladium (II) (0.257 g, 0.0003 mol) were added. The mixture was degassed for 30 min, potassium acetate (12.3 g, 0.126 mol) was added and the mixture was stirred at 105° C. over night.

The reaction mixture was cooled down to room temperature and filtered (silica/Florsil®/celite, dichloromethane) and the filtrate was concentrated under reduce pressure. The residue was dissolved in a mixture of dichloromethane: hexane, filtered (silica/Florsil®, 80% dichloromethane: hexane) and the solvent was evaporated under reduced pressure to give the desired product 2,7-boronic acid pinacol ester-9,9-bis(5'-pentyl-bicyclo[4.2.0]octa-1",3",5"-triene-7"-yl)fluorene (Monomer 2) as a pale yellow foam. Purification by recrystallisation (acetoniltrile/toluene and isopropanol/toluene), followed by a precipitation from dichloromethane and methanol gave product 2,7-boronic acid pinacol ester-9,9-bis(5'-pentyl-bicyclo[4.2.0]octa-1",3",5"-triene-7"-yl)fluorene (Monomer 2) as a white solid (11.05 g, 69% yield, purity: 96.67% by HPLC).

$^1$H NMR (600 MHz, $CDCl_3$): δ=0.58 (m, 4H), 1.09 (m, 4H), 1.20 (m, 4H), 1.38 (s, 24H), 1.47 (m, 4H), 2.03 (m, 4H), 2.61 (d, J=13.9 Hz, 2H), 3.21 (dd, J=13.9 Hz, 5.2 Hz, 2H), 3.29 (m, 2H), 6.97 (d, J=6.8 Hz, 2H), 7.01 (d, J=7.8 Hz, 2H), 7.12 (m, 4H), 7.73 (d, J=7.5 Hz, 2H), 7.67 (s, 2H), 7.82 (d, J=7.5 Hz, 2H).

Polymer Example 1

A polymer was prepared by Suzuki polymerisation of the following monomers in the following molar percentages according to the method described in WO 00/53656:

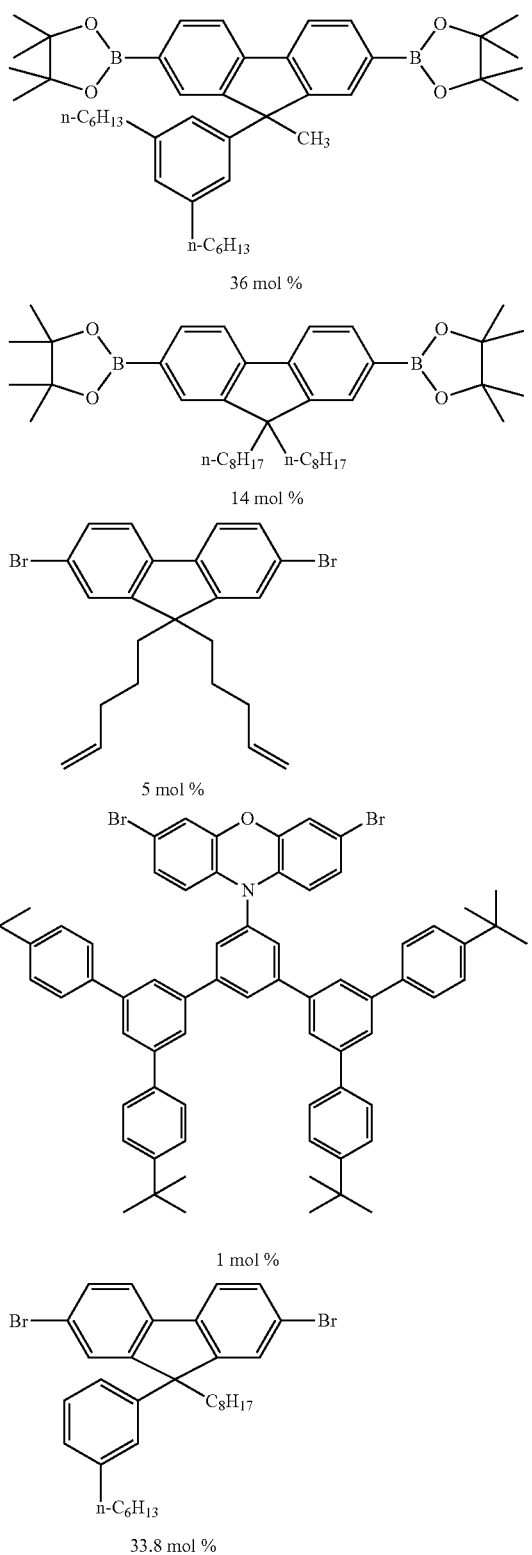

-continued

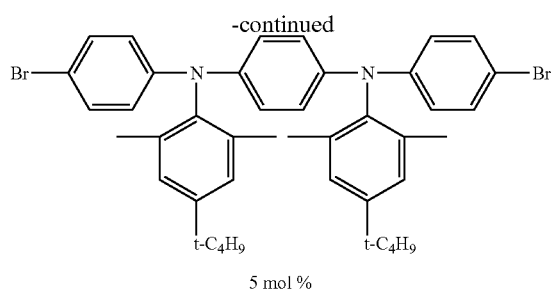

5 mol %

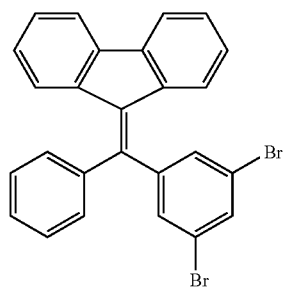

0.2 mol %

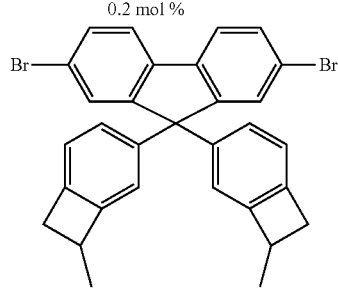

Monomer 1, 5 mol %

The polymer had a peak molecular weight (Mp) of 1,096,000.

Comparative Polymer 1

A polymer was prepared as described with reference to Polymer Example 1 except that 2,7-Dibromo-9,9-bis(bicyclo[4.2.0]octa-1,3,5-triene-3-yl)fluorene, illustrated below was used in place of Monomer 1:

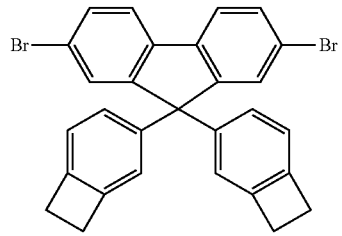 [SMILES: Brc1ccc2c(c1)C(c1ccc3c(c1)CC3)(c1ccc3c(c1)CC3)c1cc(Br)ccc1-2]

The polymer had a peak molecular weight (Mp) of 1,011,000.

Polymer Example 2

A polymer was prepared by Suzuki polymerisation of the following monomers in the following molar percentages according to the method described in WO 00/53656:

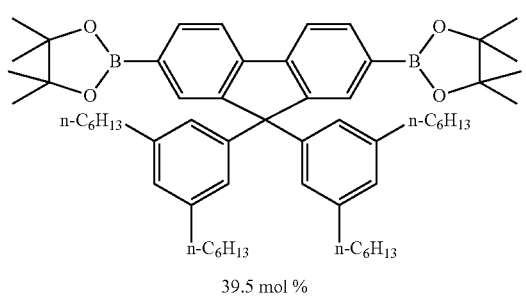

39.5 mol %

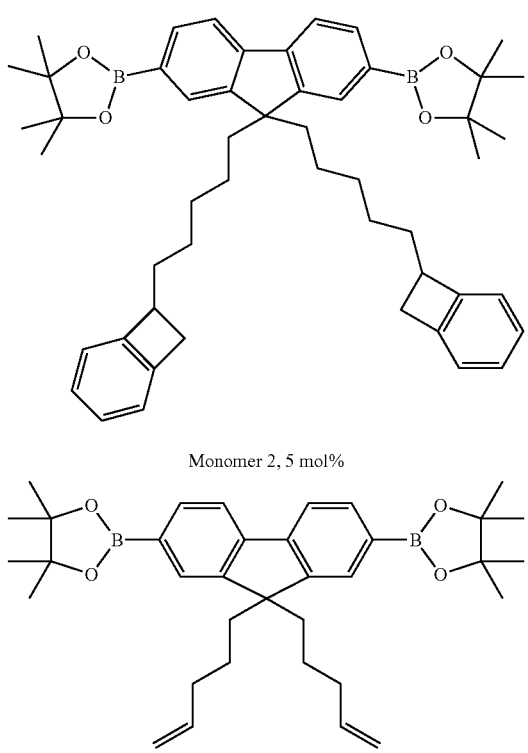

Monomer 2, 5 mol%

5 mol %

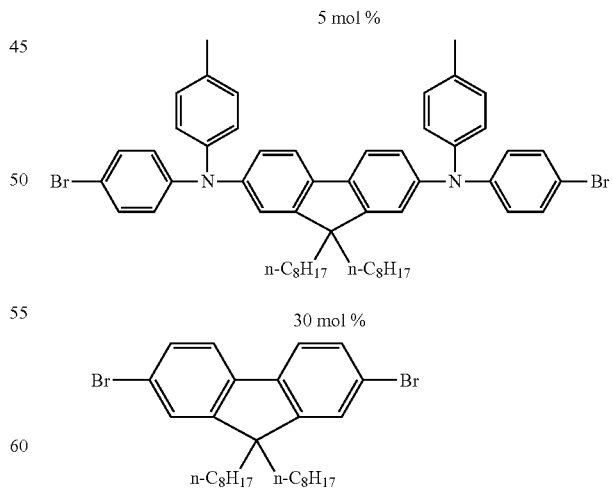

The polymer had a weight average molecular weight (Mw) of 609,000.

Comparative Polymer 2

The following polymer was prepared by Suzuki polymerisation of the following monomers in the following molar percentages according to the method described in WO 00/53656 for the purpose of comparison with Polymer Example 2:

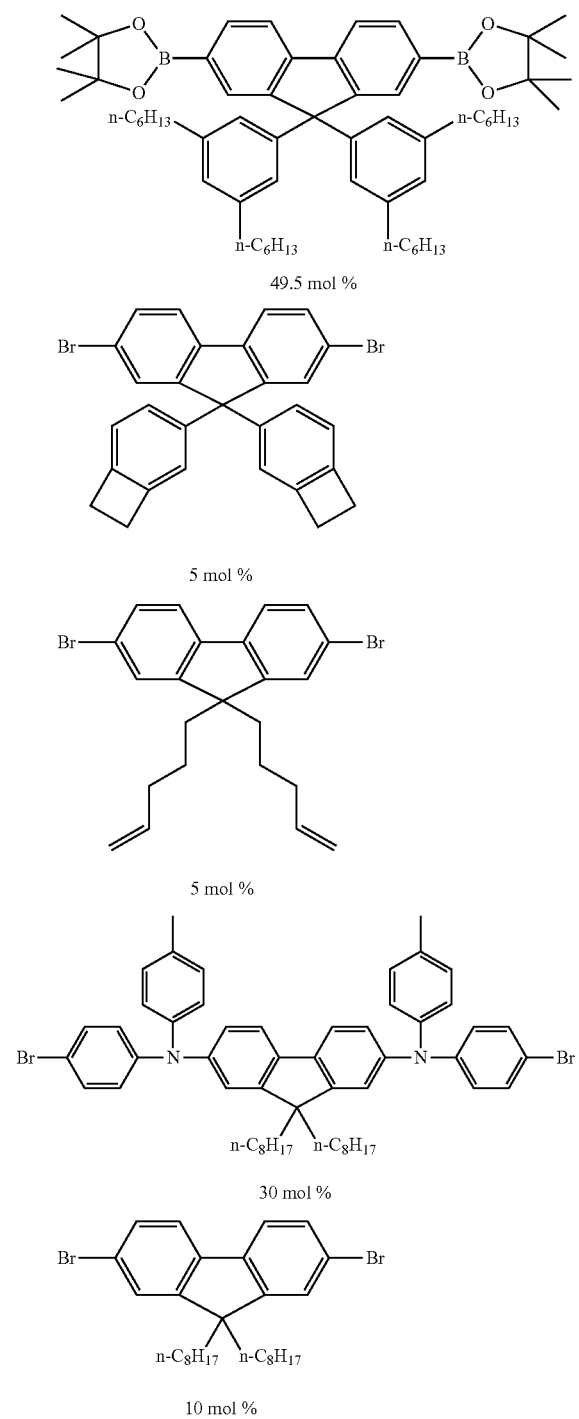

49.5 mol %

5 mol %

5 mol %

30 mol %

10 mol %

The polymer had a weight average molecular weight (Mw) of 701,000.

Polymer Example 3

A polymer was prepared as described with reference to Polymer Example 2, except the polymer was prepared with a lower weight average molecular weight (Mw) of 305,000.

Comparative Polymer 3

A polymer was prepared as described with reference to Comparative Polymer 2, except the polymer was prepared with a lower weight average molecular weight (Mw) of 376,000.

Polymer Example 4

Polymer Example 4 was prepared by Suzuki polymerisation of the following monomers in the following molar percentages according to the method described in WO 00/53656:

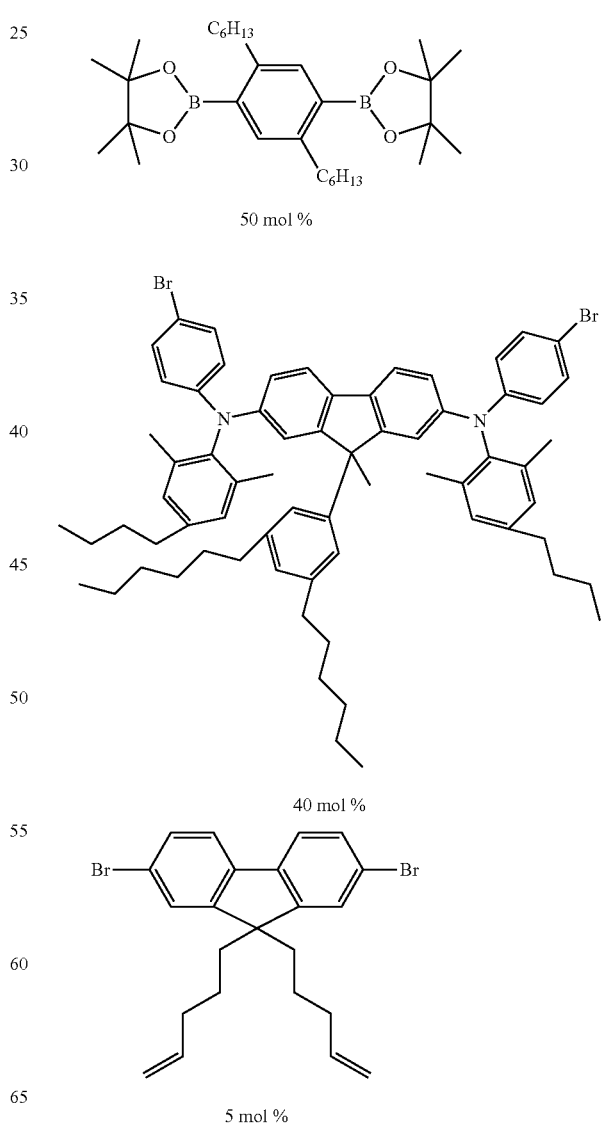

50 mol %

40 mol %

5 mol %

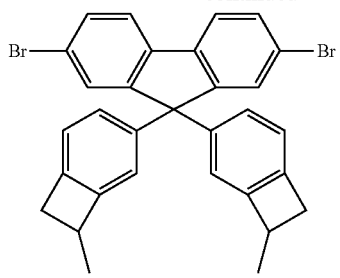

Monomer 1, 5 mol %

The polymer had a weight average molecular weight of 265,000, a peak average molecular weight of 199,000 and a number average molecular weight of 43,000.

Comparative Polymer 4

A polymer was prepared as described for Polymer Example 4 except that 2,7-Dibromo-9,9-bis(bicyclo[4.2.0]octa-1,3,5-trien-3-yl)fluorene, illustrated below was used in place of Monomer 1:

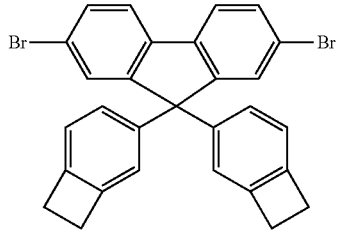

The polymer had a weight average molecular weight of 153,000, a peak average molecular weight of 139,000 and a number average molecular weight of 37,000.

Polymer Example 6

Polymer Example 6 was prepared by Suzuki polymerisation of the following monomers in the following molar percentages according to the method described in WO 00/53656:

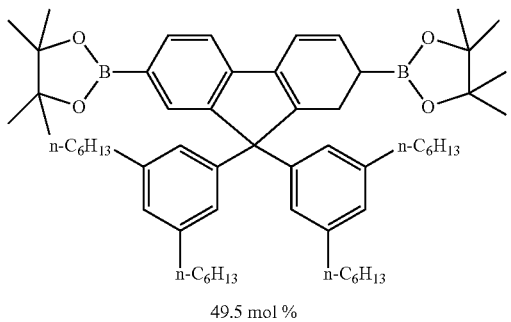

49.5 mol %

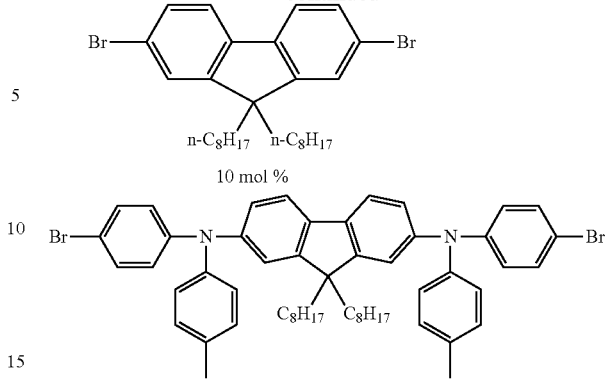

10 mol %

30 mol %

5 mol %

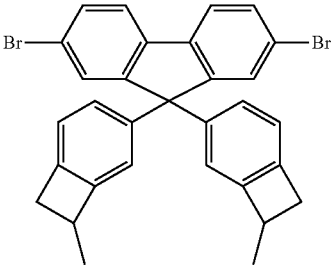

Monomer 1, 5 mol %

Polymer Example 6 had a viscosity average molecular weight of 600,000, a weight average molecular weight of 302,000, a peak average molecular weight of 248,000, a number average molecular weight of 67,000 and a polydispersity of 4.50.

Comparative Polymer 6

A polymer was prepared as described with reference to Polymer Example 6 except that Monomer 1 was replaced with 5 mol % of the following monomer:

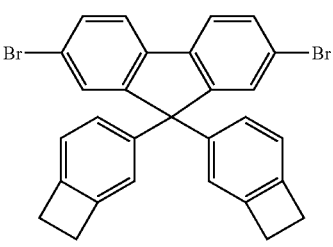 [SMILES: Brc1ccc2c(c1)C(c1ccc3c(c1)CC3)(c1ccc3c(c1)CC3)c1cc(Br)ccc1-2]

Comparative Polymer 6 had a viscosity average molecular weight of 634,000, a weight average molecular weight of 287,000, a peak average molecular weight of 188,000, a number average molecular weight of 72,000 and a polydispersity of 3.99.

Polymer Crosslinking Examples (A) Polymer Example 1

A film of Polymer Example 1 was deposited by spin-coating from a mixed xylene solution of about 1 w/v % onto a glass substrate carrying a layer of indium tin oxide and a 35 nm layer of a hole injection material available from Plextronics, Inc. The spin-coated film was then heated to crosslink the crosslinkable groups. Following heating, the film was rinsed in the spinner with the mixed xylene solvent to remove remaining soluble material. A percentage value for the extent of crosslinking was derived from the thickness of the crosslinked film before and after solvent rinse.

A film of Comparative Polymer 1 was spin-coated and heated in the same way.

The tables below illustrate the extent of crosslinking and different times and temperatures for both Polymer Example 1 and Comparative Polymer 1.

TABLE 1

Extent of crosslinking after heating for 60 minutes at 160° C.

| Polymer | Average thickness after bake | Average thickness after rinse | Extent of crosslinking (%) |
|---|---|---|---|
| Comparative Polymer 1 | 50.9 | 45.5 | 89.3 |
| | 58.3 | 48.9 | 83.9 |
| | 61.2 | 53.8 | 88.0 |
| Polymer Example 1 | 68.2 | 65.5 | 95.9 |
| | 67.2 | 66.2 | 98.5 |
| | 69.3 | 66.1 | 95.4 |

TABLE 2

Extent of crosslinking after heating for 10 minutes at 160° C.

| Polymer | Average thickness after bake | Average thickness after rinse | Extent of crosslinking (%) |
|---|---|---|---|
| Comparative Polymer 1 | 70.3 | 51.9 | 73.9 |
| | 64.4 | 39.8 | 61.8 |
| | 66.5 | 38.4 | 57.8 |
| Polymer Example 1 | 76.1 | 68.2 | 89.7 |
| | 77.9 | 66.8 | 85.7 |
| | 72.9 | 65.3 | 89.6 |

TABLE 3

Extent of crosslinking after heating for 60 minutes at 140° C.

| Polymer | Average thickness after bake | Average thickness after rinse | Extent of crosslinking (%) |
|---|---|---|---|
| Comparative Polymer 1 | 71.3 | 39.6 | 55.6 |
| | 60.3 | 32.3 | 53.6 |
| | 61.8 | 35.7 | 57.8 |
| Polymer Example 1 | 64.0 | 45.2 | 70.6 |
| | 66.3 | 56.3 | 85.0 |
| | 67.2 | 61.5 | 91.4 |

TABLE 4

Extent of crosslinking after heating for 10 minutes at 140° C.

| Polymer | Average thickness after bake | Average thickness after rinse | Extent of crosslinking (%) |
|---|---|---|---|
| Comparative Polymer 1 | 55.3 | 18.9 | 34.1 |
| | 66.6 | 18.7 | 28.1 |
| | 61.5 | 15.0 | 24.3 |
| Polymer Example 1 | 68.7 | 50.6 | 73.7 |
| | 66.8 | 50.4 | 75.4 |

The extent of crosslinking is greater for Polymer Example 1 than for Comparative Polymer 1 in all cases, and the difference in the extent of crosslinking is greater at lower temperatures and/or shorter baking times.

(B) Polymer Example 2

Films of Polymer Example 2 and Comparative Polymer 2 were prepared as described above with reference to crosslinking examples of Polymer Example 1.

TABLE 5

Extent of crosslinking after heating for 10 minutes at 140° C.

| Polymer | Average thickness after bake | Average thickness after rinse | Extent of crosslinking (%) |
|---|---|---|---|
| Comparative Polymer 2 | 51.6 | 43.5 | 84.2 |
| | 55.1 | 39.3 | 71.3 |
| | 58.9 | 38.8 | 65.8 |
| Polymer Example 2 | 55.5 | 40.0 | 72.1 |
| | 53.9 | 36.0 | 66.7 |
| | 56.4 | 41.8 | 74.1 |

TABLE 6

Extent of crosslinking after heating for 60 minutes at 140° C.

| Polymer | Average thickness after bake | Average thickness after rinse | Extent of crosslinking (%) |
|---|---|---|---|
| Comparative Polymer 2 | 52.6 | 36.2 | 68.9 |
| | 52.0 | 37.4 | 72.0 |
| | 51.8 | 37.2 | 71.9 |
| Polymer Example 2 | 55.8 | 45.0 | 80.6 |
| | 53.4 | 46.9 | 87.9 |
| | 54.8 | 42.3 | 77.2 |

TABLE 7

Extent of crosslinking after heating for 10 minutes at 160° C.

| Polymer | Average thickness after bake | Average thickness after rinse | Extent of crosslinking (%) |
|---|---|---|---|
| Comparative Polymer 2 | 29.9 | 15.0 | 50.0 |
| | 29.8 | 17.5 | 58.7 |
| | 31.7 | 19.6 | 61.7 |
| Polymer Example 2 | 25.5 | 16.3 | 63.8 |
| | 22.7 | 15.0 | 66.1 |
| | 24.6 | 16.1 | 65.6 |

TABLE 8

Extent of crosslinking after heating for 60 minutes at 160° C.

| Polymer | Average thickness after bake | Average thickness after rinse | Extent of crosslinking (%) |
|---|---|---|---|
| Comparative Polymer 2 | 31.0 | 22.9 | 73.8 |
| | 34.7 | 27.4 | 79.0 |
| | 35.2 | 27.3 | 77.6 |
| Polymer Example 2 | 26.7 | 23.8 | 89.1 |
| | 22.3 | 20.1 | 90.1 |
| | 22.5 | 20.0 | 88.9 |

(C) Polymer Example 3

Films of Polymer Example 3 and Comparative Polymer 3 were prepared as described above with reference to crosslinking examples of Polymer Example 1.

TABLE 9

Extent of crosslinking after heating for 10 minutes at 160° C.

| Polymer | Average thickness after bake | Average thickness after rinse | Extent of crosslinking (%) |
|---|---|---|---|
| Comparative Polymer 3 | 18.4 | 1.8 | 10.0 |
| | 23.0 | 2.8 | 12.3 |
| | 18.7 | 2.2 | 11.6 |
| Polymer Example 3 | 18.5 | 5.6 | 30.4 |
| | 23.2 | 5.9 | 25.5 |
| | 19.6 | 4.8 | 24.4 |

TABLE 10

Extent of crosslinking after heating for 60 minutes at 160° C.

| Polymer | Average thickness after bake | Average thickness after rinse | Extent of crosslinking (%) |
|---|---|---|---|
| Comparative Polymer 3 | 17.7 | 7.5 | 42.5 |
| | 18.3 | 2.7 | 14.8 |
| | 17.4 | 4.7 | 27.2 |
| Polymer Example 3 | 19.0 | 11.6 | 60.8 |
| | 20.5 | 12.2 | 59.4 |
| | 22.4 | 11.9 | 53.2 |

TABLE 11

Extent of crosslinking after heating for 10 minutes at 180° C.

| Polymer | Average thickness after bake | Average thickness after rinse | Extent of crosslinking (%) |
|---|---|---|---|
| Comparative Polymer 3 | 18.2 | 9.1 | 49.8 |
| | 24.0 | 9.7 | 40.6 |
| | 20.5 | 9.3 | 45.1 |
| Polymer Example 3 | 20.4 | 8.5 | 41.7 |
| | 20.4 | 8.6 | 42.1 |
| | 17.8 | 10.6 | 59.7 |

TABLE 12

Extent of crosslinking after heating for 60 minutes at 180° C.

| Polymer | Average thickness after bake | Average thickness after rinse | Extent of crosslinking (%) |
|---|---|---|---|
| Comparative Polymer 3 | 20.3 | 9.8 | 48.4 |
| | 32.8 | 19.4 | 59.2 |
| | 19.3 | 15.9 | 82.2 |
| Polymer Example 3 | 22.2 | 13.7 | 61.8 |
| | 20.5 | 15.8 | 77.1 |

The extent of crosslinking for Polymer Examples 2 and 3 is greater than, or at least similar to, that for Comparative Polymers 2 and 3 respectively.

(D) Polymer Example 4

Films of Polymer Example 4 and Comparative Polymer 4 were prepared as described above with reference to crosslinking examples of Polymer Example 1.

TABLE 13

| | Polymer Example 4 | Comparative Polymer 4 |
|---|---|---|
| Layer formation 180° C. 10 min | 76% | 14% |
| Layer formation 180° C. 60 min | 100% | 48% |

As shown in Table 13, the extent of crosslinking for Polymer Example 4 is much higher for both relatively long and relatively short crosslinking treatment times.

The high extent of crosslinking of polymers of the invention results in less wastage of uncrosslinked polymers that may be rinsed away in subsequent solution processing steps.

The relatively high degree of crosslinking achieved at relatively short treatment time may allow for faster manufacturing of OLEDs in a production line.

A layer of low molecular weight polymeric material may be particularly susceptible to removal by exposure to a solvent, however the crosslinking units of the inventive polymers provide for greater crosslinking of these polymers.

Device Example 1

A device having the following structure was formed:
ITO/HIL/HTL/LEL/Cathode
wherein ITO is an indium-tin oxide anode supported on a glass substrate; HIL is a layer of a hole-injection material available from Plextronics, Inc.; HTL is a hole transporting layer of Hole Transporting Polymer 1 described below; LEL is a blue light-emitting layer of Polymer Example 1; and Cathode is a cathode comprising a layer of a metal fluoride, a layer of silver and a layer of aluminium.

The hole injection layer, hole-transporting layer and light-emitting layer were each formed by spin-coating. The hole-transporting layer was crosslinked by heating at 180° C. to cause crosslinking of the crosslinkable group of Hole Transporting Polymer 1 prior to spin-coating of Polymer Example 1, and the light-emitting layer was crosslinked by heating at 180° C. to cause crosslinking of the crosslinkable unit of Polymer Example 1.

Hole Transporting Polymer 1 was formed by Suzuki polymerisation of the following monomers in the following molar percentages according to the method described in WO 00/53656:

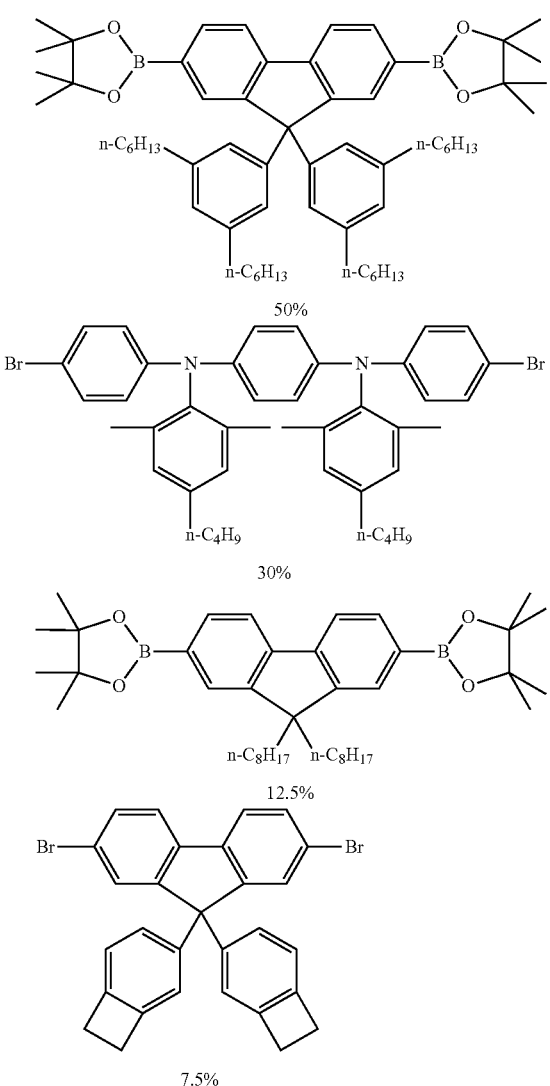

Comparative Device 1

A device was prepared as described in Device Example 1, except that Comparative Polymer 1 was used in place of Polymer Example 1.

The electroluminescent spectra, current density, external quantum efficiency and lifetimes of Device Example 1 and Comparative Device 1 were the same or similar ("lifetime" as used herein means the time taken for luminance to fall to 50% of a starting value at constant current).

Device Example 4

A device having the following structure was formed:
ITO/HIL/HTL/LEL/Cathode
wherein ITO is an indium-tin oxide anode supported on a glass substrate; HIL is a 35 nm thick layer of a hole-injection material available from Plextronics, Inc.; HTL is a 22 nm thick hole transporting layer of Polymer Example 4; LEL is a 65 nm thick blue light-emitting layer containing polymers as described below; and Cathode is a cathode comprising a layer of a metal fluoride, a layer of silver and a layer of aluminium.

The hole injection layer, hole-transporting layer and light-emitting layer were each formed by spin-coating. The hole-transporting layer was crosslinked by heating at 180° C. for 10 minutes to cause crosslinking of the crosslinkable groups of Polymer Example 4 prior to spin-coating of the materials of the light-emitting layer.

The hole injection layer was heated at 170° C. for 15 minutes prior to formation of the hole-transporting layer. The light-emitting layer was heated as 100° C. for 10 minutes.

The blue light-emitting layer was formed by spin-coating Blue Polymer 1 (90 mol %) and Additive Polymer 1 (10 mol %), followed by heating at 100° C. for 10 minutes.

Blue Polymer 1 was formed by Suzuki polymerization as described in WO 00/53656 of the following monomers:

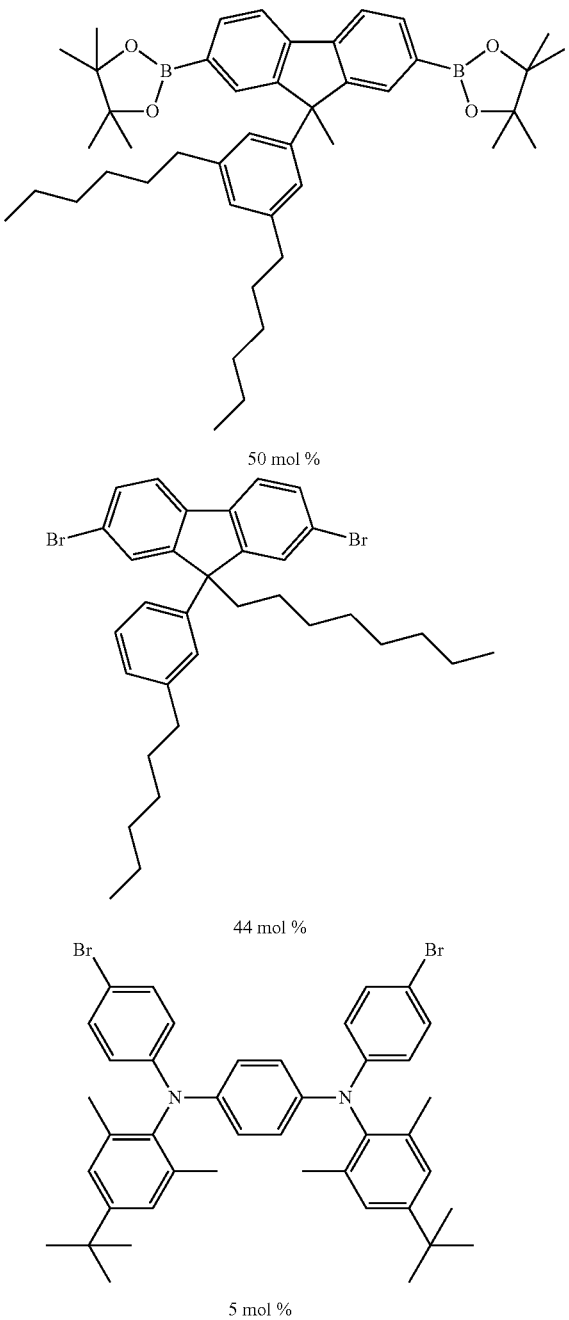

-continued

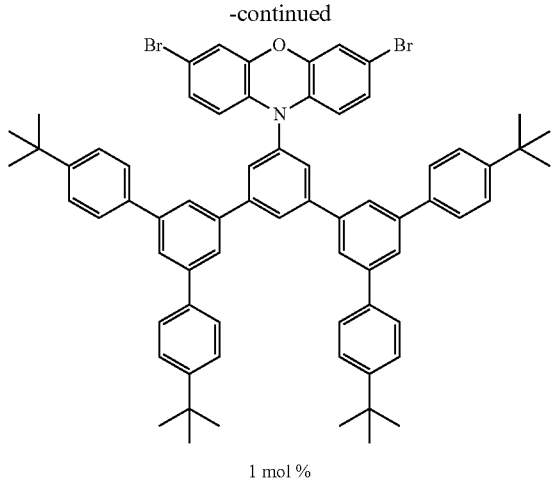

1 mol %

Additive Polymer 1 was formed by Suzuki polymerization as described in WO 00/53656 of the following monomers:

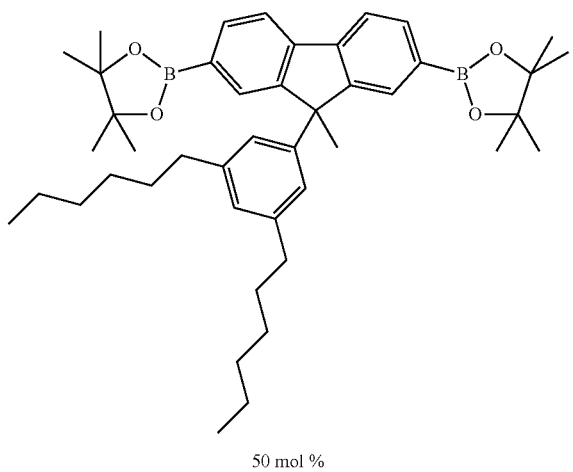

50 mol %

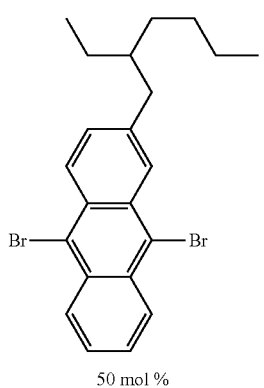

50 mol %

Comparative Device 4

A device was prepared as described in Device Example 4, except that Comparative Polymer 4 was used in place of Polymer Example 4.

TABLE 14

|  | Device Example 4 (1st test) | Device Example 4 (2nd test) | Comparative Device 4 |
|---|---|---|---|
| CIE (1931) coordinates | 0.141, 0.126 | 0.142, 0.123 | 0.143, 0.113 |
| EQE (%) | 8.6 | 8.8 | 5.7 |
| T50 (hrs) | 180 | 135 | 50 |

As shown in Table 14, colour co-ordinates of Device Example 4 and Comparative Device 4 are the same or similar. External quantum efficiency of Device Example 4 is substantially higher, and time take for luminance to fall to 50% of a starting value is much higher for Device Example 4.

Without wishing to be bound by any theory, it is believed that the improved performance of Device Example 4 is attributable to a higher degree of crosslinking of Polymer Example 4, as compared to Comparative Polymer 4, following a relatively short heating time of 10 minutes to crosslink the polymers.

Device Example 6A

A device was prepared as described in Device Example 4 except that Polymer Example 6 was used in place of Polymer Example 4 to form the hole-transporting layer, which was heated at 180° C. for 10 minutes.

The hole injection layer was formed to a thickness of 35 nm; the hole transporting layer was formed to a thickness of 22 nm; and the light-emitting layer was formed to a thickness of 65 nm.

Device Example 6B

A device was prepared as described in Device Example 6A except that the hole-transporting layer was heated at 180° C. for 60 minutes.

Comparative Devices 6A and 6B

Comparative Devices 6A and 6B were prepared as described in Device Examples 6A and 6B respectively, except that Comparative Polymer 6 was used in place of Polymer Example 6.

Data for device examples 6A and 6B and Comparative Devices 6A and 6B are set out in Table 15 in which colour and efficiency data is at a brightness of 1,000 cd/m².

TABLE 15

|  | Comparative Polymer 6 | Polymer Example 6 |
|---|---|---|
| Layer formation (%) 10 min | 15% (Comparative Device 6A) | 27% (Device Example 6A) |
| Layer formation (%) 60 min | 75% (Comparative Device 6B) | 95% (Device Example 6B) |
| Colour (CIEx) 10 min | 0.142 (Comparative Device 6A) | 0.141 (Device Example 6A) |
| Colour (CIEx) 60 min | 0.141 (Comparative Device 6B) | 0.142 (Device Example 6B) |
| Colour (CIEy) 10 min | 0.119 (Comparative Device 6A) | 0.128 (Device Example 6A) |
| Colour (CIEy) 60 min | 0.127 (Comparative Device 6B) | 0.134 (Device Example 6B) |
| EQE (%) 10 min | 6.25 (Comparative Device 6A) | 7.7 (Device Example 6A) |

TABLE 15-continued

| | Comparative Polymer 6 | Polymer Example 6 |
|---|---|---|
| EQE (%) 60 min | 7.55 (Comparative Device 6B) | 7.95 (Device Example 6B) |
| t65 (from 5k cd/m2) (hrs) 10 min | 53 (Comparative Device 6A) | 82 (Device Example 6A) |
| t65 (from 5k cd/m2) (hrs) 60 min | 80 (Comparative Device 6B) | 83 (Device Example 6B) |

Layer formation using Polymer Example 6 is higher than for Comparative Polymer 6 at both 10 minute and 60 minute treatment times, resulting in higher external quantum efficiency and longer T65 lifetime (the time taken for lifetime to fall to 65% of a starting luminance of 5,000 cd/m²).

Model Compound Synthesis

Model compounds 5a-5c were prepared according to the following reaction scheme in order to show the effect of a range of substituents R or reactivity of benzocyclobutane:

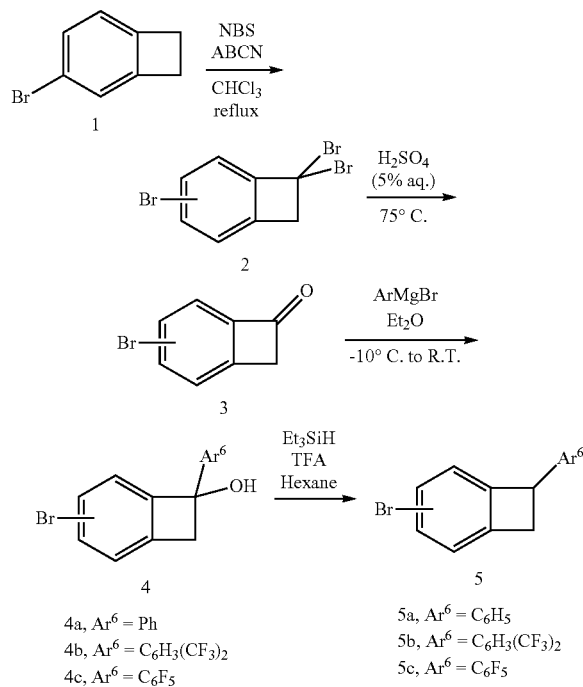

3-Bromo-7,7-dibromo-bicyclo[4.2.0]octa-1,3,5-triene (2)

To a suspension of 3-bromobicyclo[4.2.0]octa-1,3,5-triene (1) (100.0 g, 0.546 mol) in chloroform (2000 ml) at room temperature was added N-bromosuccinimide (233.4 g, 1.311 mol) followed by 1,1′-Azobis(cyanocyclohexane) (ABCN) (13.3 g, 0.054 mol). The mixture was refluxed over night.

The reaction mixture was cooled to room temperature and quenched with $H_2O$ (500 ml). The phases were separated, organic extract was washed with $H_2O$ (3×500 ml), dried over $MgSO_4$ and concentrated under reduce pressure to yield 250 g of an orange oil. The oil was filtered through a plug (silica, 90% hexane:dichloromethane) to yield 3-bromo-7,7-dibromo-bicyclo[4.2.0]octa-1,3,5-triene (2) as a pale yellow oil (178 g, GC-MS: $M^{3+}=337$, $M^+=339$, $M^-=441$, $M^{3-}=443$, main isomer in a mixture with 3-bromo-7-bromo-bicyclo[4.2.0]octa-1,3,5-triene and 3-bromo-7,7,8-tribromo-bicyclo[4.2.0]octa-1,3,5-triene), which was used without further purification in the next step.

3-Bromobicyclo[4.2.0]octa-1,3,5-triene-7-one (3)

To a suspension of 3-bromo-7,7-dibromo-bicyclo[4.2.0]octa-1,3,5-triene (2) (186.2 g, 0.546 mol, theoretical) in $H_2O$ (1000 ml) was added sulfuric acid (97%, 50 ml) at 15° C. The resulting mixture was stirred at 75° C. for 4.5 days.

The reaction mixture was cooled to room temperature was extracted with hexane (3×400 ml), the combined organic extracts were washed with NaOAc (3 wt % aq., 300 ml) and $H_2O$ (2×300 ml), dried over $MgSO_4$ and concentrated under reduce pressure to give a yellow oil. The oil was filtered through a plug (silica, gradient of hexane:dichloromethane) to yield 3-Bromobicyclo[4.2.0]octa-1,3,5-triene-7-one (3) as a pale yellow oil (55.7 g, GC-MS: $M^+=196$, $M^-=198$, 51% yield, isolated as a mixture of isomers).

$^1H$ NMR (600 MHz, $CDCl_3$): δ=3.99 (s, 2H), 7.22 (d, J=8.0 Hz, 1H), 7.58 (d, J=8.0 Hz, 1H), 7.72 (s, 1H).

General Method for the Synthesis of 3-Bromo-7-aryl-bicyclo[4.2.0]octa-1,3,5-triene 3-Bromo-7-aryl-bicyclo[4.2.0]octa-1,3,5-triene-7-ol (4)

To a solution of 3-bromobicyclo[4.2.0]octa-1,3,5-triene-7-one (3) (2.0 g, 10.1 mmol) in diethyl ether (20 ml) at −10° C. was added the aryl Grignard. The resulting mixture was stirred at room temperature for 1 hr and quenched with HCl (2M aq., 10 ml) at 0° C. Phases were separated, organic extract was washed with $H_2O$ (3×20 ml), dried over $MgSO_4$ and concentrated under reduce pressure. The residue was filtered through a plug (silica, gradient of hexane:dichloromethane) to yield 3-bromo-7-aryl-bicyclo[4.2.0]octa-1,3,5-triene-7-ol (4) as a mixture of isomers.

3-Bromo-7-aryl-bicyclo[4.2.0]octa-1,3,5-triene (5)

To a suspension of 3-bromo-7-aryl-bicyclo[4.2.0]octa-1,3,5-triene-7-ol (4) (1 eq.) in hexane at 0° C. was added triethylsilane (1.5 eq.) followed by trifluoro acetic acid (5 eq.). The resulting mixture was stirred at room temperature for 1 hr and poured into ice/water (20 ml). Phases were separated, organic extract was washed with NaOAc (10 wt % aq., 20 ml), $H_2O$ (4×20 ml), dried over $MgSO_4$ and concentrated under reduce pressure. The residue was filtered through a plug (silica, hexane) to yield 3-bromo-7-aryl-bicyclo[4.2.0]octa-1,3,5-triene (5) as a mixture of isomers.

Specific Materials

3-Bromo-7-phenyl-bicyclo[4.2.0]octa-1,3,5-triene-7-ol (4a)

Using 3-Bromobicyclo[4.2.0]octa-1,3,5-triene-7-one (3) (2.0 g, 10.1 mmol), diethyl ether (20 ml), phenyl magnesium bromide (3M in diethyl ether, 3.4 ml, 10.1 mmol) afforded 3-Bromo-7-phenyl-bicyclo[4.2.0]octa-1,3,5-triene-7-ol (4a) as a pale yellow oil (2.1 g, GC-MS: $M^+=274$, $M^+=276$, 75% yield, isolated as a mixture of isomers).

$^1H$ NMR (600 MHz, $CDCl_3$): δ=2.65 (s, 1H), 3.57 (d, J=14.3 Hz, 1H), 3.64 (d, J=14.3 Hz, 1H), 7.16 (d, J=7.9 Hz,

1H), 7.30 (m, 1H), 7.35 (m, 2H), 7.40 (s, 1H), 7.45 (d, J=8.8 Hz, 2H), 7.47 (d, J=7.8 Hz, 1H).

3-Bromo-7-(3',5'-bis(trifluoromethyl)benzyl)-bicyclo[4.2.0]octa-1,3,5-triene-7-ol (4b)

3,5-bis(trifluoromethyl)phenyl magnesium bromide was prepared from 3,5-bis(trifluoromethyl)-bromobenzene (3.27 g, 11.7 mmol) in solution in diethyl ether (3.8 ml). It was added to magnesium turning (0.30 g, 12.2 mmol) and a catalytic amount of iodine. It was refluxed for 1 hr, cooled down to room temperature and used as such.

Using 3-bromobicyclo[4.2.0]octa-1,3,5-triene-7-one (3) (2.0 g, 0.015 mol), diethyl ether (20 ml), 3,5-bis(trifluoromethyl)phenyl magnesium bromide (3M in diethyl ether, 3.8 ml, 11.7 mmol) afforded 3-Bromo-7-(3',5'-bis(trifluoromethyl)benzyl)-bicyclo[4.2.0]octa-1,3,5-triene-7-ol (4b) (3.17 g, GC-MS: $M^+$=410, $M^-$=412, 76% yield, isolated as a mixture of isomers).

3-Bromo-7-pentafluoro phenyl-bicyclo[4.2.0]octa-1,3,5-triene-7-ol (4c)

Pentafluorophenyl magnesium bromide was prepared from bromopentafluorobenzene (2.88 g, 11.7 mmol) in solution in diethyl ether (12 ml). It was added to magnesium turning (0.30 g, 12.2 mmol) and catalytic amount of iodine. It was refluxed for 1 hr, cooled down to room temperature and used as such.

Using 3-bromobicyclo[4.2.0]octa-1,3,5-triene-7-one (3) (2.0 g, 0.015 mol), diethyl ether (10 ml), pentafluorophenyl magnesium bromide (1M in diethyl ether, 12 ml, 11.7 mmol) afforded 3-Bromo-7-pentafluoro phenyl-bicyclo[4.2.0]octa-1,3,5-triene-7-ol (4c) as an oil (3.2 g, GC-MS: $M^+$=364, $M^-$=366, 86% yield, isolated as a mixture of isomers).

3-Bromo-7-phenyl-bicyclo[4.2.0]octa-1,3,5-triene (5a)

Using 3-bromo-7-phenyl-bicyclo[4.2.0]octa-1,3,5-triene-7-ol (4a) (2.1 g, 7.6 mmol), hexane (10 ml), triethylsilane (1.3 g, 11.5 mmol), trifluoro acetic acid (4.3 g, 38.2 mmol) afforded 3-Bromo-7-phenyl-bicyclo[4.2.0]octa-1,3,5-triene (5a) as a pale yellow oil (1.5 g, GC-MS: $M^+$=258, $M^-$=260, 76% yield, isolated as a mixture of isomers).

$^1$H NMR (600 MHz, CDCl$_3$): δ=3.06 (dd, J=14.2 Hz, 1.8 Hz, 1H), 3.71 (dd, J=14.2 Hz, 5.6 Hz, 1H), 4.62 (m, 1H), 7.03 (d, J=7.7 Hz, 1H), 7.23 (m, 3H), 7.31 (m, 3H), 7.42 (d, J=7.8 Hz, 1H).

3-Bromo-7-(3',5'-bis(trifluoromethyl)benzyl)-bicyclo[4.2.0]octa-1,3,5-triene (5b)

Using 3-Bromo-7-(3',5'-bis(trifluoromethyl)benzyl)-bicyclo[4.2.0]octa-1,3,5-triene (4b) (3.2 g, 7.7 mmol), hexane (10 ml), triethylsilane (1.3 g, 11.5 mmol), trifluoro acetic acid (4.4 g, 38.6 mmol) afforded 3-Bromo-7-(3',5'-bis(trifluoromethyl)benzyl)-bicyclo[4.2.0]octa-1,3,5-triene (5b) (0.8 g, GC-MS: $M^+$=394, $M^-$=396, 26% yield, isolated as a mixture of isomers).

$^1$H NMR (600 MHz, CDCl$_3$): δ=3.11 (dd, J=14.3 Hz, 2.5 Hz, 1H), 3.81 (dd, J=14.3 Hz, 5.7 Hz, 1H), 4.72 (m, 1H), 7.05 (d, J=7.9 Hz, 1H), 7.36 (s, 1H), 7.48 (d, J=7.8 Hz, 1H), 7.66 (s, 2H), 7.76 (s, 1H).

3-Bromo-7-pentafluoro phenyl-bicyclo[4.2.0]octa-1,3,5-triene (5c)

Using 3-Bromo-7-pentafluoro phenyl-bicyclo[4.2.0]octa-1,3,5-triene-7-ol (4c) (3.1 g, 8.5 mmol), hexane (15 ml), triethylsilane (1.08 g, 9.34 mmol), trifluoro acetic acid (9.7 g, 84.9 mmol) afforded 3-Bromo-7-pentafluoro phenyl-bicyclo[4.2.0]octa-1,3,5-triene (5c) (2.7 g, GC-MS: $M^+$=348, $M^-$=351, 73% yield, isolated as a mixture of isomers).

$^1$H NMR (600 MHz, CDCl$_3$): δ=3.43 (dd, J=14.3 Hz, 2.8 Hz, 1H), 3.76 (dd, J=14.3 Hz, 5.7 Hz, 1H), 4.86 (m, 1H), 6.99 (d, J=7.9 Hz, 1H), 7.30 (s, 1H), 7.41 (d, J=7.8 Hz, 1H).

Reactivity of Model Compounds

The relative reactivity of the model compounds in a Diels-Alder-type reaction with compound 6 in the following reaction scheme below was determined:

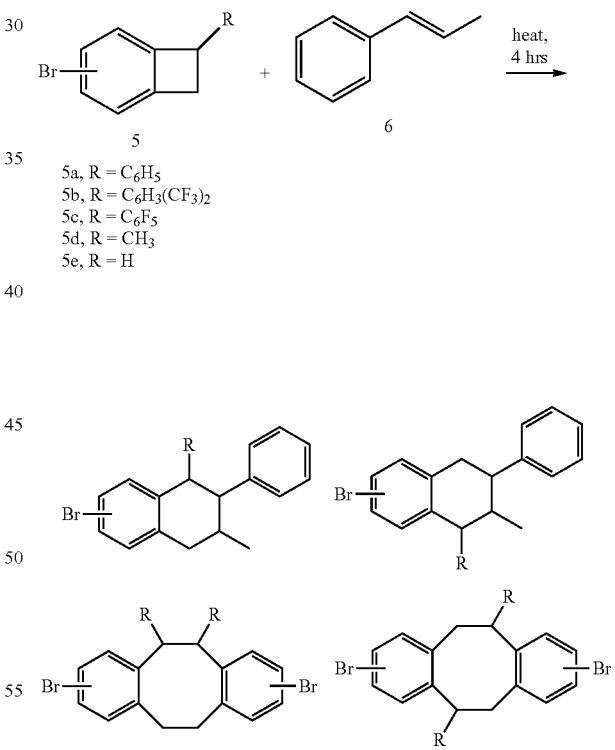

5a, R = C$_6$H$_5$
5b, R = C$_6$H$_3$(CF$_3$)$_2$
5c, R = C$_6$F$_5$
5d, R = CH$_3$
5e, R = H

The reactions were carried out by mixing the model compound (0.1 mmol) and trans-beta-methylstyrene (0.1 mmol, 0.118 g, Compound 6). The reaction mixture was stirred at the temperature given in the table below for 4 hrs under a nitrogen atmosphere.

Relative reactivity was measured by measuring the percentage of the reacted model compound by GC-MS.

| Name | | | | | |
|---|---|---|---|---|---|
| 5a (R = C$_6$H$_5$) | 5b (R = C$_6$H$_3$(CF$_3$)$_2$) | 5c (R = C$_6$F$_5$) | | 5d (R = CH$_3$) | 5e (R = H) |
| | | Structure | | | |
| | | | | | |
| 160° C. | 100% | — | — | 13.4-15.1% | 0.5-0.6% |
| 140° C. | 100% | 91% | 76% | 1.6% | — |
| 120° C. | 65% | — | 29% | — | — |

Results at 160° C. show that substituted model compounds 5a and 5d are more reactive than unsubstituted model compound 5e.

Results at lower temperatures show particularly high reactivity of substituted model compounds, in particular for model compounds substituted by phenyl (including both unsubstituted and substituted phenyl).

Although the invention has been described above with reference to crosslinked polymers and their formation for use in OLEDs, it will be appreciated that the invention is applicable to other organic electronic devices comprising crosslinked polymers including, without limitation, organic photoresponsive devices include photovoltaic devices and photosensors; organic thin film transistors; and organic memory array devices.

Moreover, it will be appreciated that the invention is applicable outside the field of organic electronic devices. For example, the method of the present invention may be used to crosslink polymers for use in products that require high resistance to deformation, for example Kevlar. A compound comprising at least two crosslinkable groups of Formula (I), for example a compound of formula (IIa) or (IIb), may be reacted with a polymer to form a crosslinked polymer for such applications.

Compounds of formula (IIa) or (IIb) may also be monomers. These monomers may be polymerized with one or more comonomers containing reactive groups capable of reacting with groups of formula (I), for example comonomers containing dienophile groups. Alternatively, the compounds of formula (IIa) or (IIb) may be polymerized directly with one another in the case where compound of formula (IIa) or (IIb) includes one or more dienophiles for reaction with a diene formed by ring-opening of the cyclobutane ring of formula (I). The one or more dienophile units may be provided as group A of Formula (IIa) or (IIb), and each dienophile unit may be a group comprising a carbon-carbon double bond. Polymers formed by polymerisation of compounds of formula (IIa) or (IIb), either alone or with comonomers, may or may not be crosslinked depending on the number of groups of formula (I) and/or the number of dienophile groups present.

Polymers formed by polymerisation of compound of formula (IIa) or (IIb) may be used as, for example, the gate dielectric of an organic thin film transistor or to form the planarization layer of a display backplane, for example an OLED or LCD backplane. This may allow formation of a planarization layer on a plastic substrate (e.g. for formation of a flexible device), in particular plastics that may not be suitable for processing at high temperatures. An exemplary monomer of this type is illustrated below:

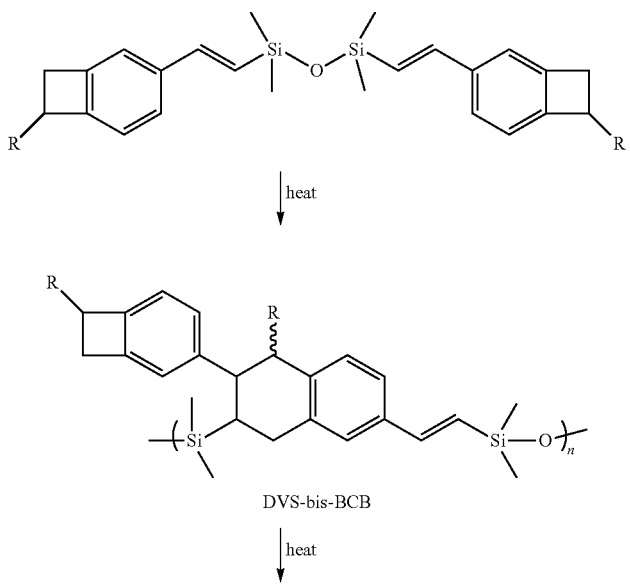

DVS-bis-BCB

-continued

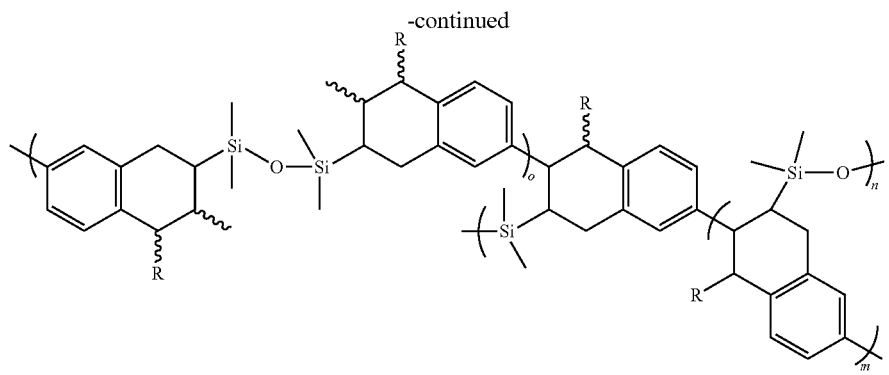

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A method of forming a crosslinked polymer having a conjugated polymer backbone, the method comprising the step of reacting a crosslinkable group in the presence of a polymer, wherein:

the crosslinkable group comprises a core unit substituted with at least one crosslinkable unit of formula (I):

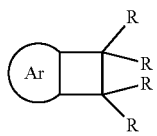

(I)

the crosslinkable group is a repeat unit of the polymer of formula (IIIa) or (IIIb):

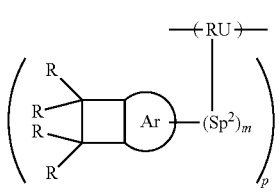

(IIIa)

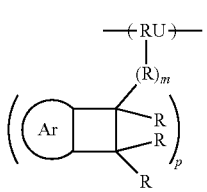

(IIIb)

wherein:
RU represents a conjugated core repeat unit comprised in a backbone of the polymer, wherein RU is at least partially conjugated to one or both adjacent repeat units in the polymer backbone;
$Sp^2$ represents a spacer group;
m is 0 or 1;
p is at least 1;

Ar is aryl or heteroaryl which is unsubstituted or is substituted with one or more substituents independently selected from monovalent substituents and a divalent linking group linking the unit of formula (I) to the core unit; and R is independently in each occurrence H, a monovalent substituent, or a divalent linking group linking the unit of formula (I) to the core unit, with the proviso that at least one R is a linear or branched $C_{3-20}$ alkyl, and wherein the polymer backbone is substituted with a crosslinkable double bond unit.

2. A method according to claim 1 wherein Ar is phenyl.

3. A method according to claim 2 wherein the at least one unit of formula (I) has formula (Ia):

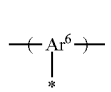

(Ia)

4. A method according to claim 1 wherein only one R is not H.

5. A method according to claim 1 wherein the crosslinkable group comprises at least two units of formula (I).

6. A method according to claim 1 wherein the crosslinkable group is a crosslinkable compound mixed with the polymer.

7. A method according to claim 1 wherein RU has formula (XVI):

$$-\!\!\!\left(\!\!Ar^6\!\!\right)\!\!\!-$$
$$\underset{*}{|}$$

(XVI)

wherein $Ar^6$ represents a substituted or unsubstituted aryl or heteroaryl group and * represents a bond to $Sp^2$, Ar or R.

8. A method according to claim 7 wherein $Ar^6$ is selected from the group consisting of phenyl, fluorene and indenofluorene, each of which is substituted or unsubstituted.

9. A method according to claim 1 wherein the repeat unit of formula (IIIa) or (IIIb) has formula (IIIc):

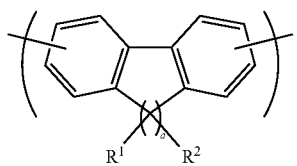

(IIIc)

wherein $R^1$ and $R^2$ are independently in each occurrence H or a substituent with the proviso that at least one of $R^1$ and $R^2$ has formula $-(Sp^2)_m$-XL; XL is a crosslinkable unit of formula (I); and a is at least 1.

10. A method according to claim 1 wherein $Sp^2$ is selected from the group consisting of a $C_{1-20}$ n-alkyl chain and an optionally substituted aryl or heteroaryl, and wherein one or more non-adjacent C atoms of the n-alkyl chain are optionally replaced with optionally substituted aryl or heteroaryl, O, S, substituted N, substituted Si, —C=O, or —COO—, and one or more H atoms of the n-alkyl chain are optionally replaced with $C_{1-5}$ alkyl, F, or an aryl or heteroaryl group.

11. A method according to claim 1 wherein the reaction is performed by heating the reactants or exposing the reactants to UV light.

12. A method according to claim 11 wherein the reaction is performed at a temperature of less than 180° C.

13. A method according to claim 1 wherein the repeat units of formula (IIIa) or (IIIb) form up to 25 mol % of the repeat units of the polymer.

14. A method according to claim 1 wherein the crosslinkable double bond unit is a group of formula (V):

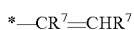

*—CR$^7$=CHR$^7$      (V), wherein $R^7$ independently in each occurrence is H or a substituent and * is a point of attachment of the crosslinkable double bond unit to the polymer backbone, and wherein the group of formula (V) is bound directly to the polymer backbone or is spaced apart therefrom by a spacer group.

15. A method of forming a crosslinked polymer comprising the step of reacting a crosslinkable group in the presence of a polymer, wherein:
the crosslinkable group comprises a core unit substituted with at least one crosslinkable unit of formula (I):

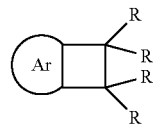

(I)

the crosslinkable group is a repeat unit of the polymer of formula (IIIa) or (IIIb):

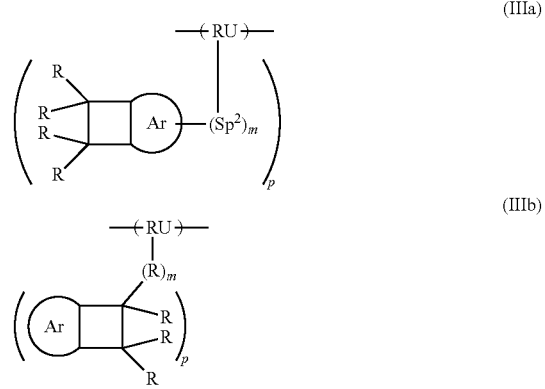

(IIIa)

(IIIb)

wherein:
RU represents a conjugated core repeat unit comprised in a backbone of the polymer, wherein RU is at least partially conjugated to one or both adjacent repeat units in the polymer backbone;
$Sp^2$ represents a spacer group;
m is 0 or 1;
p is at least 1;
Ar is aryl or heteroaryl which is unsubstituted or is substituted with one or more substituents independently selected from monovalent substituents and a divalent linking group linking the unit of formula (I) to the core unit; and
R is independently in each occurrence H, a monovalent substituent, or a divalent linking group linking the unit of formula (I) to the core unit, with the proviso that at least one R is a branched $C_{3-20}$ alkyl.

* * * * *